(12) United States Patent
Norton et al.

(10) Patent No.: US 10,578,469 B2
(45) Date of Patent: *Mar. 3, 2020

(54) AUTOMATED SET-UP FOR CELL SORTING

(71) Applicant: Becton, Dickinson and Company, Franklin Lakes, NJ (US)

(72) Inventors: Pierce O. Norton, Los Gatos, CA (US); Vladimir Azersky, San Jose, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/918,862

(22) Filed: Mar. 12, 2018

(65) Prior Publication Data

US 2018/0202846 A1    Jul. 19, 2018

Related U.S. Application Data

(63) Continuation of application No. 14/251,207, filed on Apr. 11, 2014, now Pat. No. 9,952,076.

(60) Provisional application No. 61/811,465, filed on Apr. 12, 2013.

(51) Int. Cl.
| | |
|---|---|
| *G05D 7/06* | (2006.01) |
| *G01F 1/66* | (2006.01) |
| *G01N 15/14* | (2006.01) |
| *G06T 7/00* | (2017.01) |
| *G01N 15/10* | (2006.01) |

(52) U.S. Cl.
CPC .............. *G01F 1/661* (2013.01); *G01N 15/14* (2013.01); *G01N 15/1404* (2013.01); *G01N 15/1459* (2013.01); *G05D 7/0617* (2013.01); *G06T 7/0012* (2013.01); *G01N 2015/1006* (2013.01); *G01N 2015/1406* (2013.01); *G01N 2015/149* (2013.01); *G01N 2015/1481* (2013.01)

(58) Field of Classification Search
None
See application file for complete search history.

(56) References Cited

U.S. PATENT DOCUMENTS

| | | |
|---|---|---|
| 438,483 A | 10/1890 | McGary |
| 3,960,449 A | 6/1976 | Carleton et al. |
| 4,009,435 A | 2/1977 | Hogg |

(Continued)

FOREIGN PATENT DOCUMENTS

| | | |
|---|---|---|
| CN | 101382499 A | 3/2009 |
| CN | 101923036 A | 12/2010 |

(Continued)

OTHER PUBLICATIONS

Godin et al. "Adjustable flow cytometer". 2007IEEE, pp. 117-118.*

(Continued)

*Primary Examiner* — Van H Nguyen
(74) *Attorney, Agent, or Firm* — Bret E. Field; Bozicevic, Field & Francis LLP

(57) ABSTRACT

Apparatus and methods are described for automatically performing set-up steps for flow cytometry operations. The invention provides for the spatial determination of a flow stream and the subsequent automatic alignment of analysis devices and/or collection vessels. The automatic determination of flow stream properties provides for the automatic configuration flow cytometer parameters.

18 Claims, 3 Drawing Sheets

(56) References Cited

U.S. PATENT DOCUMENTS

| | | | |
|---|---|---|---|
| 4,318,481 A * | 3/1982 | Lombardo | G01N 15/1404 209/3.1 |
| 4,347,935 A | 9/1982 | Merrill | |
| 4,487,320 A | 12/1984 | Auer | |
| 4,667,830 A | 5/1987 | Nozaki et al. | |
| 4,981,580 A | 1/1991 | Auer | |
| 5,155,543 A * | 10/1992 | Hirako | G01N 15/1431 356/343 |
| 5,451,525 A | 9/1995 | Shenkin | |
| 5,464,581 A | 11/1995 | Van Den Engh | |
| 5,483,469 A | 1/1996 | Van Den Engh | |
| 5,602,039 A | 2/1997 | Van Den Engh | |
| 5,643,796 A | 7/1997 | Van Den Engh | |
| 5,700,692 A | 12/1997 | Sweet | |
| 5,916,449 A | 6/1999 | Ellwart et al. | |
| 5,998,212 A | 12/1999 | Corio et al. | |
| 6,079,836 A | 6/2000 | Burr et al. | |
| 6,133,044 A | 10/2000 | Van Den Engh | |
| 6,248,590 B1 | 6/2001 | Malachowski | |
| 6,372,506 B1 | 4/2002 | Norton | |
| 6,589,792 B1 | 7/2003 | Malachowski | |
| 6,746,873 B1 | 6/2004 | Buchanan | |
| 6,809,804 B1 | 10/2004 | Yount et al. | |
| 6,890,487 B1 | 5/2005 | Skylar | |
| 7,221,453 B2 | 5/2007 | Sharpe | |
| 7,242,474 B2 | 7/2007 | Cox | |
| 7,417,734 B2 | 8/2008 | Kanda | |
| 7,658,121 B2 | 2/2010 | Zhao et al. | |
| 7,880,108 B2 | 2/2011 | Schembri et al. | |
| 8,213,009 B2 | 7/2012 | Muraki | |
| 8,262,990 B2 | 9/2012 | Bair et al. | |
| 8,290,625 B2 | 10/2012 | Degeal | |
| 8,436,993 B2 | 5/2013 | Kaduchak | |
| 8,685,418 B2 | 4/2014 | Thompson et al. | |
| 8,709,825 B2 | 4/2014 | Durack | |
| 8,975,595 B2 | 3/2015 | Norton | |
| 9,013,692 B2 | 4/2015 | Hu | |
| 9,366,616 B2 | 6/2016 | Norton | |
| 2005/0110996 A1 | 5/2005 | Sharpe | |
| 2005/0227362 A1 | 10/2005 | Lary et al. | |
| 2008/0255705 A1 | 10/2008 | Degeal | |
| 2009/0061513 A1 | 3/2009 | Andersson et al. | |
| 2010/0120077 A1 | 5/2010 | Daridon et al. | |
| 2011/0033339 A1 | 2/2011 | Muraki et al. | |
| 2011/0069310 A1 | 3/2011 | Muraki et al. | |
| 2011/0090500 A1 | 4/2011 | Hu | |
| 2011/0221892 A1 | 9/2011 | Neckels et al. | |
| 2011/0259749 A1 | 10/2011 | Kanda | |
| 2011/0267604 A1 | 11/2011 | Swalwell | |
| 2012/0064100 A1 | 3/2012 | Barry et al. | |
| 2012/0140205 A1 | 6/2012 | Kaduchak | |
| 2012/0301869 A1 | 11/2012 | Evans | |
| 2013/0224787 A1 | 8/2013 | Durack | |
| 2013/0258075 A1 | 10/2013 | Muraki et al. | |
| 2013/0327957 A1 | 12/2013 | Ayliffe | |
| 2013/0340539 A1 | 12/2013 | Gaskill-Fox | |
| 2014/0144871 A1 | 5/2014 | Hoshimoto et al. | |

FOREIGN PATENT DOCUMENTS

| | | |
|---|---|---|
| JP | S62151742 | 7/1987 |
| JP | H09196855 | 7/1997 |
| JP | H10507525 | 7/1998 |
| JP | 2002505423 | 2/2002 |
| JP | 2004518127 | 6/2004 |
| JP | 2006504970 | 2/2006 |

OTHER PUBLICATIONS

Huang et al "Continuous Cell Sorting and Interacttve Cell Handling on Channel-Less Chips Using Image Dielectrophoresis", 2005 IEEE, pp. 1696-1699.*

Kovac, et al. "Image-based Cell Sorting Using Optofluidics", 2008 IEEE, pp. 193-194.

Lamonaca, et al. "Synchronization in the Image Flow Cytometer", 2011 IEEE, pp. 505-508.

Lin, et al. "A Novel Micro Flow Cytometer With 3-Dimensional Focusing Utilizing Dielectrophoretic and Hydrodynamic Forces", 2003 IEEE, pp. 439-442.

Wang, et al. "Cell Sorting with Combined Optical Tweezers and Microfluidic Chip Technologies", 2010 IEEE, pp. 201-206.

"BD FACSARIA II Operator Guideline", "Doc88" online text sharing platform, www.doc88.com/p-384749989686.html, downloaded Aug. 27, 2018, 354 pages, 2009.

* cited by examiner

AUTOMATED SET-UP FOR CELL SORTING

CROSS-REFERENCE TO RELATED APPLICATIONS

This application is a continuation application of U.S. patent application Ser. No. 14/251,207 filed Apr. 11, 2014, now U.S. Pat. No. 9,952,076, which application, pursuant to 35 U.S.C. § 119 (e), claims priority to the filing date of U.S. Provisional Patent Application Ser. No. 61/811,465 filed Apr. 12, 2013, the disclosures of which applications are herein incorporated by reference.

INTRODUCTION

Flow cytometers known in the art are used for analyzing and sorting particles in a fluid sample, such as cells of a blood sample or particles of interest in any other type of biological or chemical sample. A flow cytometer typically includes a sample reservoir for receiving a fluid sample, such as a blood sample, and a sheath reservoir containing a sheath fluid. The flow cytometer transports the particles (hereinafter called "cells") in the fluid sample as a cell stream to a flow cell, while also directing the sheath fluid to the flow cell.

Within the flow cell, a liquid sheath is formed around the cell stream to impart a substantially uniform velocity on the cell stream. The flow cell hydrodynamically focuses the cells within the stream to pass through the center of a laser beam in a flow cell. The point at which the cells intersect the laser beam is commonly known as the interrogation point. As a cell moves through the interrogation point, it causes the laser light to scatter. The laser light also excites components in the cell stream that have fluorescent properties, such as fluorescent markers that have been added to the fluid sample and adhered to certain cells of interest, or fluorescent beads mixed into the stream. The flow cytometer includes an appropriate detection system consisting of photomultiplier tubes, photodiodes or other light detecting devices, which are focused at the intersection point. The flow cytometer analyzes the detected light to measure physical and fluorescent properties of the cell. The flow cytometer can further sort the cells based on these measured properties. The flow stream exits the flow cell via a nozzle with a nozzle diameter that is appropriate for the fluidics system and sort rate desired.

To sort cells by an electrostatic method, the desired cell must be contained within an electrically charged droplet. To produce droplets, the flow cell is rapidly vibrated by an acoustic device, such as a piezoelectric element. The volume of a droplet is conventionally estimated by the hydrodynamic properties of the flow stream and the nozzle dimensions. To charge the droplet, the flow cell includes a charging element whose electrical potential can be rapidly changed. Because the cell stream exits the flow cell in a substantially downward vertical direction, the droplets also propagate in that direction after they are formed. Droplets, whether they are charged or are uncharged must be collected in a sample collection vessel that is appropriately directed to collect the one or more flow streams generated by the deflection plates. Accordingly, the droplets and the cells contained therein may be collected in appropriate collection vessels downstream of the plates.

Known flow cytometers similar to the type described above are described, for example, in U.S. Pat. Nos. 3,960,449, 4,347,935, 4,667,830, 5,464,581, 5,483,469, 5,602,039, 5,643,796 and 5,700,692, the entire contents of each patent being incorporated by reference herein. Other types of known flow cytometer are the FACSVantage™, FACSort™, FACSCount™, FACScan™, and FACSCalibur™ systems, each manufactured by Becton Dickinson and Company, the assignee of the present invention.

Although this method generally enables the flow cytometer to dispense sorted cells into collection vessels and therefore sort the cells of interest with reasonable accuracy, the method requires a substantial amount of user input at the time of set-up. The flow stream and collection vessels are conventionally manually aligned. The fluidics parameters such as flow rate and sheath fluid composition must be matched with an appropriate nozzle diameter.

SUMMARY

Aspects of the present disclosure include systems for adjusting one or more parameters of a flow cytometer. Systems according to certain embodiments include an imaging sensor configured to capture one or more images of a detection field of a flow stream of the flow cytometer and a processor configured to generate a data signal from the one or more captured images such that the system adjusts one or more parameters of the flow cytometer in response to the data signal.

In certain embodiments, the subject systems are configured to reduce the need for user input or manual adjustment during sample analysis with a flow cytometer. In some embodiments, systems of interest may be partially or fully automated so that adjustments to parameters of a flow cytometer are processor controlled. In certain embodiments, the subject systems are configured to adjust one or more parameters of the flow cytometer without any human input.

In certain embodiments, the present disclosure provides a system for automatically localizing a stream position in a liquid flow from a flow cytometer comprising a first camera, adapted to detect a stream position in a first detection field and to generate a first signal representative of the stream position and a first stage wherein the first stage is operationally connected to the first camera and configured to move in an XY plane in response to the first signal.

The system may further include a second camera adapted to detect a steam position in a second detection field and to generate a second signal representative of the stream position wherein the first and second detection fields of the first and second cameras are substantially orthogonally oriented in the XY plane wherein the first stage is operationally connected to the second camera and configured to move the XY plane in response to the second signal in addition to the first signal. In some embodiments a laser is mounted or collection device is mounted on the first stage.

In some embodiments the system may include a second stage wherein a collection device is mounted on the second stage and the second stage is configured to move in the XY plane in response to the first signal and the second signal. The system may further comprise an electrical system configured to adjust an electrical charge on the flow stream in response to the second signal from the second camera. The operational connection between the cameras and the stages may be mediated by a processor connected to the first camera and the first and second camera and the first stage and wherein the processor is configured to receive the signals from the first and second cameras and calculate an optimum position for the first stage. In some embodiments the operational connection is mediated by a processor connected to the first and second camera and the second stage and configured to receive the signals from the first and second cameras and calculate an optimum position for the second stage. In some embodiments the stream may include a series of drops.

A system according to certain embodiments is provided for automatically determining a nozzle opening diameter with a first camera, adapted to detect a stream dimension in a first detection field and to generate a first signal representative of the stream dimension and a processor having memory with instructions thereon configured to determine a value for the nozzle opening diameter from the stream dimension and transmit the value to a flow cytometer. The stream dimension may be the width of the stream. In some embodiments the flow cytometer may be configured to automatically adjust a series of parameters after receiving the transmitted value. The series of parameters may be selected from the group comprising hydrostatic pressure, drop charge, deflection voltage, charge correction value, drop delay, drop frequency, drop amplitude, and charge phase.

Aspects of the disclosure also include methods for adjusting one or more parameters of a flow cytometer. Methods according to certain embodiments include capturing one or more images of a flow stream of the flow cytometer in a detection field, determining one or more properties of the flow stream in the detection field, generating a data signal corresponding to the one or more properties of the flow stream and adjusting one or more parameters of the flow cytometer in response to the data signal.

Aspects of the present disclosure also include computer controlled systems for practicing the subject methods, where the systems further include one or more computers having processors configured to automate one or more steps of the methods described herein. In some embodiments, systems include a computer having a computer readable storage medium with a computer program stored thereon, where the computer program when loaded on the computer includes instructions for capturing one or more images of a flow stream of the flow cytometer in a detection field; algorithm for determining the spatial position of the flow stream in the detection field; algorithm for generating a data signal corresponding to the spatial position of the flow stream; and instructions for adjusting one or more parameters of the flow cytometer in response to the data signal. In certain instances, systems include a computer having a computer readable storage medium with a computer program stored thereon, where the computer program when loaded on the computer includes instructions for capturing one or more images of a flow stream of the flow cytometer in a detection field; algorithm for determining the physical dimensions of the flow stream in the detection field; algorithm for generating a data signal corresponding to the physical dimensions of the flow stream; and instructions for adjusting one or more parameters of the flow cytometer in response to the data signal.

BRIEF DESCRIPTION OF THE FIGURES

The invention may be best understood from the following detailed description when read in conjunction with the accompanying drawings. Included in the drawings are the following figures.

DETAILED DESCRIPTION

Figure 1:
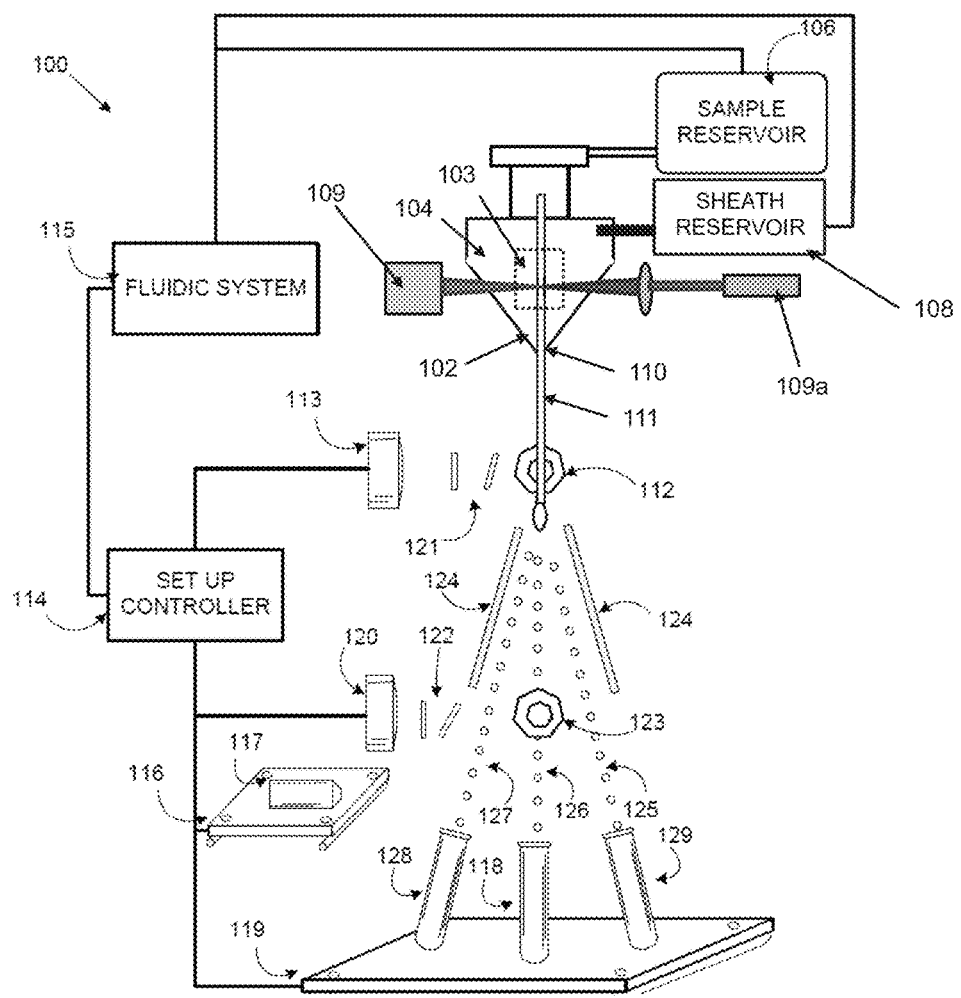
FIG. 1 depicts a schematic illustration of a system according to certain embodiments.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As summarized above, the present disclosure provides systems configured to automate adjustments of one or more parameters of a flow cytometer. In further describing embodiments of the disclosure, systems configured to adjust one or more parameters of a flow cytometer are first described in greater detail. Next, methods for adjusting one or more parameters of a flow cytometer with the subject systems are described. Computer controlled systems which automate adjustments to one or more parameters of a flow cytometer are also provided.

Systems for Adjusting Parameters of a Flow Cytometer

Aspects of the present disclosure include systems configured to adjust parameters of a flow cytometer. The term "adjusting" is used herein in its conventional sense to refer to changing one or more functional parameters of the flow cytometer. As described in greater detail below, the desired adjustment may vary in terms of goal, where in some instances the desired adjustments are adjustments that ultimately result in enhanced efficiency of some desirable parameter, e.g., improved cell sorting accuracy, enhanced particle collection, identifying component malfunction (e.g., clogged flow cell nozzle), energy consumption, particle charging efficiency, more accurate particle charging, enhanced particle deflection during cell sorting, among other adjustments. In embodiments, the subject systems are configured to reduce the need for user input or manual adjustment during sample analysis with a flow cytometer. In certain embodiments, systems of interest may be fully automated so that adjustments to parameters of a flow cytometer are processor controlled. By "fully automated" is meant that adjustments made in response to data signals corresponding to one or more parameters of the flow stream and derived from one or more captured images of the flow stream requires little to no human intervention or manual input into the subject systems. In certain embodiments, the subject systems are configured to adjust one or more parameters of the flow cytometer based on the data signals corresponding to one or more parameters of the flow stream without any human intervention.

As summarized above, systems include one or more imaging sensors configured to capture images of a flow cytometer flow stream in one or more detection fields. By "detection field" is meant the region of the flow stream which is imaged by the one or more imaging sensors. Detection fields may vary depending on the properties of the flow stream being interrogated. In embodiments, the detection field may span 0.001 mm or more of the flow stream, such as 0.005 mm or more, such as 0.01 mm or more, such as 0.05 mm or more, such as 0.1 mm or more, such as 0.5 mm or more, such as 1 mm or more, such as 2 mm or more, such as 5 mm or more and including 10 mm or more of the flow stream. For example, where the subject systems are configured to determine a physical dimension (e.g., width) of the flow stream, the detection field may be a planar cross-section of the flow stream. In another example, where the subject systems are configured to determine the spatial position of the flow stream, the detection field may be a predetermined length of the flow stream, such as for example to determine the angle made by the flow stream with respect to the axis of the flow cell nozzle.

The detection field interrogated by the subject systems may vary depending on the parameter of the flow cytometer being adjusted. In some embodiments, the detection field includes the flow cell nozzle orifice. In other embodiments, the detection field includes the location of the flow stream where the drops containing the particles of interest are charged (i.e., the "break-off" point where the continuous flow stream begins to form discrete droplets). In yet other embodiments, the detection field includes the region where charged particles are deflected by deflector plates during cell sorting.

Systems include one or more imaging sensors configured to capture images of a flow stream in a detection field. The imaging sensor may be any suitable device capable of capturing and converting an optical image into an electronic data signal, including but not limited to charge-coupled devices, semiconductor charge-coupled devices (CCD), active pixel sensors (APS), complementary metal-oxide semiconductor (CMOS) image sensors or N-type metal-oxide semiconductor (NMOS) image sensors. In some embodiments, the imaging sensor is a CCD camera. For example, the camera may be an electron multiplying CCD (EMCCD) camera or an intensified CCD (ICCD) camera. In other embodiments, the imaging sensor is a CMOS-type camera.

Depending on the number of detection fields being interrogated and flow cytometer parameters of interest, the number of imaging sensors in the subject systems may vary, as desired. For example, the subject systems may include one imaging sensor or more, such as two imaging sensors or more, such as three imaging sensors or more, such as four imaging sensors or more, such as five imaging sensors or more and including ten imaging sensors or more. In certain embodiments, systems include one imaging sensor. In other embodiments, systems include two imaging sensors. Where systems include more than one imaging sensor, each imaging sensors may be oriented with respect to the other (as referenced in an X-Y plane) at an angle ranging from 10° to 90°, such as from 15° to 85°, such as from 20° to 80°, such as from 25° to 75° and including from 30° to 60°. In certain embodiments, each imaging sensor is oriented orthogonally (as referenced in an X-Y plane) to each other. For example, where the subject systems include two imaging sensors, the first imaging sensor is oriented orthogonally (as referenced in an X-Y plane) to the second imaging sensor.

Where the subject systems include more than one imaging sensor, each imaging sensor may be the same or a combination of sensors. For example, where the subject systems include two imaging sensors, in some embodiments the first imaging sensor is a CCD-type device and the second imaging sensor is a CMOS-type device. In other embodiments, both the first and second imaging sensor are CCD-type devices. In yet other embodiments, both the first and second imaging sensors are CMOS-type devices.

In some embodiments, the imaging sensors are stationary, maintaining a single position within the flow cytometer. In other embodiments, the imaging sensors may be configured to move along the path of the flow stream. For instance, the imaging sensor may be configured to move upstream and downstream alongside the flow stream capturing images in a plurality of detection fields. For example, systems may include an imaging sensor which is adapted to capture images in two or more different detection fields along the flow stream, such as 3 or more detection fields, such as 4 or more detection fields and including 5 or more detections fields. Where the imaging sensor is configured to move along the flow stream, the imaging sensor may be moved along the flow stream path continuously or in discrete intervals. In some embodiments, the imaging sensor is displaced continuously. In other embodiments, the imaging sensor may be displaced along the flow stream path in discrete intervals, such as for example in 1 mm or greater increments, such as 2 mm or greater increments and including 5 mm or greater increments.

Where the imaging sensor is configured to capture images at different positions along a path of the flow stream, the imaging sensor may be configured to capture images continuously or in discrete intervals. In some instances, imaging sensors of interest are configured to capture images continuously. In other instances, imaging sensors are configured to take measurements in discrete intervals, such as capturing an image of the flow stream every 0.001 millsecond, every 0.01 millsecond, every 0.1 millsecond, every 1 millsecond, every 10 millseconds, every 100 millseconds and including every 1000 millseconds, or some other interval.

As described in greater detail below, the imaging sensor is configured to capture one or more images of the flow stream in each detection field. For example, the imaging sensor may be configured to capture 2 or more images of the flow stream in each detection field, such as 3 or more images, such as 4 or more images, such as 5 or more images, such as 10 or more images, such as 15 or more images and including 25 or more images. Where a plurality of images are captured in a detection field, the processor (as discussed below) may include digital imaging processing algorithm for stitching together the plurality of images.

Depending on the flow stream rate and desired image resolution, the imaging sensor may have an exposure time of 100 ms or less when reading out the full sensor, such as 75 ms or less, such as 50 ms or less, such as 25 ms or less, such 10 ms or less, such as 5 ms or less, such as 1 ms or less, such as 0.1 ms or less such as 0.01 ms or less, such as 0.001 ms or less, such as 0.0001 ms or less, such as 0.00001 ms or less and including an exposure time of 0.000001 ms or less. For example, the exposure time of the imaging sensor in a detection field which captures images of the flow stream at the flow cell nozzle orifice may have an exposure time which ranges from 0.0001 ms to 10 ms, such as from 0.001 ms to 5 ms, such as from 0.01 ms to 2 ms and including from 0.1 ms to 1 ms. The exposure time of imaging sensors in a detection field which captures images of the flow cytometer flow stream downstream from the nozzle orifice may have an exposure time which ranges from 0.0001 ms to 10 ms, such as from 0.001 ms to 5 ms, such as from 0.01 ms to 2 ms and including from 0.1 ms to 1 ms.

In certain embodiments, imaging sensors in the subject systems may have 1M active pixels or more, such as 1.5M or more, e.g., 2M or more, 2.5M or more, or 3M or more. In certain aspects, a pixel corresponds to an actual physical dimension of about 0.3 μm. Depending on the detection field, in some instances, imaging sensors have a sensor area of 150 mm$^2$ or more, such as about 150 mm$^2$ to about 175 mm$^2$, about 175 mm$^2$ to about 200 mm$^2$, 200 mm$^2$ to about 225 mm$^2$, about 225 mm$^2$ to about 250 mm$^2$, about 250 mm$^2$ to about 300 mm$^2$, about 300 mm$^2$ to about 400 mm$^2$, about 400 mm$^2$ to about 500 mm$^2$, about 500 mm$^2$ to about 750 mm$^2$, about 750 mm$^2$ to about 1000 mm$^2$, or about 1000 mm$^2$ or more.

The imaging sensor may be positioned at any suitable distance from the flow cytometer flow stream so long as the detection field is capable of capturing an image of the flow stream. For example, the imaging sensor may be positioned 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow cytometer flow stream.

In some embodiments, the imaging sensor is positioned at an angle with respect to the flow stream axis. For example, the imaging sensor may be positioned at an angle with respect to the axis of the flow stream which ranges from 10° to 90°, such as from 15° to 85°, such as from 20° to 80°, such as from 25° to 75° and including from 30° to 60°. In certain embodiments, the imaging sensor is positioned at a 90° angle with respect to the axis of the flow stream.

In some instances, the imaging sensor also includes an optical adjustment protocol. By "optical adjustment" is meant that capturing images of the detection field by the imaging sensor may be changed as desired, such as to increase or decrease the captured dimensions or to enhance the optical resolution of the image. In some instances, optical adjustment is a magnification protocol configured to increase the size of the detection field captured by the imaging sensor, such as by 5% or greater, such as by 10% or greater, such as by 25% or greater, such as by 50% or greater and including increasing the detection field of the imaging sensor by 75% or greater. In other instances, optical adjustment is a de-magnification protocol configured to decrease the size of the detection field captured by the imaging sensor, such as by 5% or greater, such as by 10% or greater, such as by 25% or greater, such as by 50% or greater and including decreasing the width of the slit shaped beam by 75% or greater. In certain embodiments, optical adjustment is an enhanced resolution protocol configured to improve the resolution of the captured images, such as by 5% or greater, such as by 10% or greater, such as by 25% or greater, such as by 50% or greater and including enhancing the resolution of the captured images by 75% or greater. Capturing images of the detection field by the imaging sensor may be adjusted with any convenient optical adjustment protocol, including but not limited to lens, mirrors, filters and combinations thereof. In certain embodiments, the imaging sensor includes a focusing lens. The focusing lens, for example may be a de-magnifying lens. In other embodiments, the focusing lens is a magnifying lens.

Imaging sensors of the present disclosure may also include one or more wavelength separators. The term "wavelength separator" is used herein in its conventional sense to refer to an optical protocol for separating polychromatic light into its component wavelengths for detection. Wavelength separation, according to certain embodiments, may include selectively passing or blocking specific wavelengths or wavelength ranges of the polychromatic light. To separate wavelengths of light, the transmitted light may be passed through any convenient wavelength separating protocol, including but not limited to colored glass, bandpass filters, interference filters, dichroic mirrors, diffraction gratings, monochromators and combinations thereof, among other wavelength separating protocols. Depending on the detection field, light source and flow stream being visualized, systems may include one or more wavelength separators, such as two or more, such as three or more, such as four or more, such as five or more and including 10 or more wavelength separators. In one example, imaging sensors include one bandpass filter. In another example, imaging sensors include two or more bandpass filters. In another example, imaging sensors include two or more bandpass filters and a diffraction grating. In yet another example, imaging sensors include a plurality of bandpass filters and a monochromator. In certain embodiments, imaging sensors include a plurality of bandpass filters and diffraction gratings configured into a filter wheel setup. Where imaging sensors include two or more wavelength separators, the wavelength separators may be utilized individually or in series to separate polychromatic light into component wavelengths. In some embodiments, wavelength separators are arranged in series. In other embodiments, wavelength separators are arranged individually such that one or more measurements are conducted using each of the wavelength separators.

In some embodiments, systems include one or more optical filters, such as one or more bandpass filters. For example, in some instances the optical filters of interest are bandpass filters having minimum bandwidths ranging from 2 nm to 100 nm, such as from 3 nm to 95 nm, such as from 5 nm to 95 nm, such as from 10 nm to 90 nm, such as from 12 nm to 85 nm, such as from 15 nm to 80 nm and including bandpass filters having minimum bandwidths ranging from 20 nm to 50 nm. In other instances, the optical filters are longpass filters, such as for example longpass filters which attenuate wavelengths of light of 1600 nm or less, such as 1550 nm or less, such as 1500 nm or less, such as 1450 nm or less, such as 1400 nm or less, such as 1350 nm or less, such as 1300 nm or less, such as 1000 nm or less, such as 950 nm or less, such as 900 nm or less, such as 850 nm or less, such as 800 nm or less, such as 750 nm or less, such as 700 nm or less, such as 650 nm or less, such as 600 nm or less, such as 550 nm or less, such as 500 nm or less and including a longpass filter which attenuates wavelengths of light of 450 nm or less. In yet other instances, the optical filters are shortpass filters, such as for example shortpass filters which attenuate wavelengths of light of 200 nm or greater, such as 250 nm or greater, such as 300 nm or greater, such as 350 nm or greater, such as 400 nm or greater, such as 450 nm or greater, such as 500 nm or greater, such as 550 nm or greater and including shortpass filters which attenuate wavelengths of light of 600 nm or greater.

In other embodiments, the wavelength separator is a diffraction grating. Diffraction gratings may include, but are not limited to transmission, dispersive or reflective diffraction gratings. Suitable spacings of the diffraction grating may vary depending on the configuration of the light source, detection field and imaging sensor and other optical adjust protocols present (e.g., focusing lens), ranging from 0.01 µm to 10 µm, such as from 0.025 µm to 7.5 µm, such as from 0.5 µm to 5 µm, such as from 0.75 µm to 4 µm, such as from 1 µm to 3.5 µm and including from 1.5 µm to 3.5 µm.

In some embodiments, each imaging sensor is operably coupled to one or more light sources for illuminating the flow stream in the detection field. In some embodiments, the light source is a broadband light source, emitting light having a broad range of wavelengths, such as for example, spanning 50 nm or more, such as 100 nm or more, such as 150 nm or more, such as 200 nm or more, such as 250 nm or more, such as 300 nm or more, such as 350 nm or more, such as 400 nm or more and including spanning 500 nm or more. For example, one suitable broadband light source emits light having wavelengths from 200 nm to 1500 nm. Another example of a suitable broadband light source includes a light source that emits light having wavelengths from 400 nm to 1000 nm. Any convenient broadband light source protocol may be employed, such as a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof.

In other embodiments, the light source is a narrow band light source emitting a particular wavelength or a narrow range of wavelengths. In some instances, the narrow band light sources emit light having a narrow range of wavelengths, such as for example, 50 nm or less, such as 40 nm or less, such as 30 nm or less, such as 25 nm or less, such as 20 nm or less, such as 15 nm or less, such as 10 nm or less, such as 5 nm or less, such as 2 nm or less and including light sources which emit a specific wavelength of light (i.e., monochromatic light). Any convenient narrow band light source protocol may be employed, such as a narrow wavelength LED, laser diode or a broadband light source coupled to one or more optical bandpass filters, diffraction gratings, monochromators or any combination thereof.

The subject systems may include one or more light sources, as desired, such as two or more light sources, such as three or more light sources, such as four or more light sources, such as five or more light sources and including ten or more light sources. The light source may include an combination of types of light sources, for example, where two lights sources are employed, a first light source may be a broadband white light source (e.g., broadband white light LED) and second light source may be a broadband near-infrared light source (e.g., broadband near-IR LED). In other instances, where two light sources are employed, a first light source may be a broadband white light source (e.g., broadband white light LED) and the second light source may be a narrow spectra light source (e.g., a narrow band visible light or near-IR LED). In yet other instances, the light source is an plurality of narrow band light sources each emitting specific wavelengths, such as an array of two or more LEDs, such as an array of three or more LEDs, such as an array of five or more LEDs, including an array of ten or more LEDs.

In some embodiments, light sources emit light having wavelengths ranging from 200 nm to 1500 nm, such as from 250 nm to 1250 nm, such as from 300 nm to 1000 nm, such as from 350 nm to 900 nm and including from 400 nm to 800 nm. For example, the light source may include a broadband light source emitting light having wavelengths from 200 nm to 900 nm. In other instances, the light source includes a plurality of narrow band light sources emitting wavelengths ranging from 200 nm to 900 nm. For example, the light source may be plurality of narrow band LEDs (1 nm-25 nm) each independently emitting light having a range of wavelengths between 200 nm to 900 nm. In some embodiments, the narrow band light source is one or more narrow band lamps emitting light in the range of 200 nm to 900 nm, such as a narrow band cadmium lamp, cesium lamp, helium lamp, mercury lamp, mercury-cadmium lamp, potassium lamp, sodium lamp, neon lamp, zinc lamp or any combination thereof.

In certain embodiments, the light source is a stroboscopic light source where the flow stream is illuminated with periodic flashes of light. Depending on the light source (e.g., flash lamp, pulsed laser) the frequency of light strobe may vary, and may be 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 kHz or greater, such as 25 kHz or greater, such as 50 kHz or greater and including 100 kHz or greater. In these embodiments, the strobe light may be operably coupled to a processor having a frequency generator which regulates strobe frequency. In some instances, the frequency generator is coupled to the droplet drive generator such that the strobe light is synchronized with droplet generation. In other instances, the frequency generator of the strobe light is operably coupled to the one or more optical sensors such that the frequency of the strobe light is synchronized with the frequency of image capture. In certain instances, suitable strobe light sources and frequency controllers include, but are not limited to those described in U.S. Pat. Nos. 5,700,692 and 6,372,506, the disclosures of which are herein incorporated by reference. Strobing and pulsed light sources are also described in Sorenson, et al. *Cytometry*, Vol. 14, No. 2, pages 115-22 (1993); Wheeless, et al. *The Journal of Histochemestry and Cytochemistry*, Vol. 24, No. 1, pages 265-268 (1976), the disclosures of which are herein incorporated by reference.

As summarized above, systems include one or more processors operably coupled to the imaging sensors where the processors are configured to generate a data signal from the captured images and to adjust one or more parameters of the flow cytometer in response to the data signal. In embodiments, the processor is configured to execute instructions from memory to adjust one or more parameters of the flow cytometer based on the data signal derived from the captured images. Parameters of the flow cytometer which may be adjusted according to embodiments of the present disclosure include, but are not limited to hydrostatic pressure, drop charging voltage, deflection plate voltage, charge correction value, drop delay, drop drive frequency, drop amplitude and charge phase. In certain embodiments, the processor is operably coupled to one or more support stages and the positioning of the support stages may be adjusted in response to the data signal derived from the captured images.

In embodiments, the processors include memory having a plurality of instructions for performing the steps of the subject methods (as described in greater detail below), such as illuminating a flow cytometer flow stream in a detection field with a light source, capturing one or more images of the flow stream, generating a data signal corresponding to one or more properties of the flow stream based on the captured images, and adjusting parameters of the flow cytometer in response to the data signal. The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system. The processor includes memory having instructions stored thereon for performing the steps of the subject methods including illuminating a flow cytometer flow stream in a detection field with a light source, capturing one or more images of the flow stream, generating a data signal corresponding to one or more properties of the flow stream based on the captured images, and adjusting parameters of the flow cytometer in response to the data signal.

In embodiments, the processor is configured to generate a data signal corresponding to one or more properties of the flow stream from the captured images. In detection fields where the flow stream is continuous, the processor may be configured to generate a data signal corresponding to the spatial position of the flow stream, the dimensions of the flow stream such as flow stream width, as well as flow rate and flow turbulence. In detection fields where the flow stream is composed of discrete droplets, the processor may be configured to generate a data signal corresponding to the spatial position of the flow stream, drop size including drop diameter and volume, drop drive frequency, drop amplitude as well as the uniformity of drop size and frequency. In certain embodiments, the processor may be configured to generate a data signal corresponding to the ratio of the size of the flow stream as compared to the expected size of the flow stream based on empirical characteristics of the flow cytometer and user inputted data. In other embodiments, the processor may be configured to assess the captured images to determine whether a flow stream is present or absent in a particular detection field. In yet other embodiments, the processor may be configured to assess the captured images of the flow stream to determine the flow cell nozzle orifice size.

In some embodiments, the processor is operably coupled to an imaging sensor which captures images of the flow stream in a detection field and generates a data signal corresponding to the spatial position of the flow stream. For instance, the processor may take the captured images of the flow stream in the detection field and map the spatial position of the flow stream in an X-Y plane. In some instances, the position of the flow stream in the X-Y plane is compared to the spatial position of the vertical axis of the flow cell nozzle to determine position of the flow stream with respect to the vertical axis formed by the flow cell nozzle. Based on the determined spatial position of the flow stream in the detection field, the processor generates a data signal corresponding to the spatial position of the flow stream.

In these embodiments, the data signal corresponding to the spatial position of the flow stream may be used by the processor to automatically adjust one or more parameters of the flow cytometer. In some instances, the data signal is used to adjust the position of a support stage having one or more containers for collecting particles, such as for cell sorting. In certain embodiments, the processor generates a data signal corresponding to the position of the flow stream and adjusts the position of a support stage so that the collection containers on the support stage are aligned with the trajectory of the flow stream. For example, the processor may be configured to map the position of the flow stream in each detection field in an X-Y plane, map the position of the container in the X-Y plane and match the position of the container in the X-Y plane with the position of the flow stream in the X-Y plane to align the collection container with the flow stream. In some instances, the subject systems are configured to map the position of the flow stream in two detection fields. In these instances, the processor maps the spatial position of the flow stream in the first detection field in an X-Y plane and maps the spatial position of the flow stream in the second detection field in the X-Y plane. Based on the mapped positions of the flow stream in the first and second detection fields, the processor is configured to generate a data signal corresponding to the spatial position of the flow stream in the flow cytometer.

In these embodiments, the processor generates a data signal corresponding to the spatial position of the flow stream and automatically adjusts the position of a support stage in an X-Y plane so as to optimize collection of the flow stream. For example, optimizing collection may include reducing the number of flow stream particles not collected by the containers on the support stage due to misalignment of the flow stream with the collection containers. For example, the number of particles not collected by containers on the support stage due to misalignment is reduced by 5% or more as compared to a container on a support stage not adjusted in response to the data signal, such as by 10% or more, such as 15% or more, such as 20% or more, such as 25% or more, such as 35% or more, such as 50% or more, such as 75% or more, such as 90% or more, such as 95% or more and including by 99% or more. Put another way, the processer in certain instances automatically aligns the position of the support stage in response to data signal corresponding to the spatial position of the flow stream so that the number of particles collected by the container is increased by 5% or more as compared to a container on a support stage not adjusted in response to the data signal, such as by 10% or more, such as 15% or more, such as 20% or more, such as 25% or more, such as 35% or more, such as 50% or more, such as 75% or more, such as 90% or more, such as 95% or more and including by 99% or more. In other instances, adjusting the position of the support stage having containers for collecting charged particles during cell sorting may be increased as compared to collection with a support stage not adjusted in response to the data signal by 2 fold or greater, such as 3 fold or greater, such as 5 fold or greater and including by 10 fold or greater.

In some embodiments, a support stage is positioned downstream from deflector plates and includes containers for collecting sorted cells that have been separated based on charge (i.e., positive, negative and neutral). In some instances, the support structure may include three or more containers. In other instances, the support structure includes a single container partitioned into three or more compartments for collecting the sorted cells. An imaging sensor is configured to capture images of the flow stream in a detection field downstream from the deflector plates and a processor operably coupled to the imaging sensor generates a data signal corresponding to the spatial positions of the flow streams. In these embodiments, the processor takes the captured images of each flow stream and maps the spatial position of the flow stream in an X-Y plane. In some instances, the position of the flow stream in the X-Y plane is compared to the position of the flow stream before entering the deflector plates to determine the deviation due to the effects of the deflector plates. In these embodiments, the processor may generate a distinct data signal corresponding to the position of the flow stream of neutral particles, the flow stream of negative particles and the flow stream of positive particles, or any combination thereof. In one example, the processor generates a data signal which corresponds to the flow stream position of neutral particles after deflection by the deflector plates. In another example, the processor generates a data signal which corresponds to the flow stream position of negative particles after deflection by the deflector plates. In yet another example, the processor generates a data signal which corresponds to the flow stream position of positive particles coming from the deflector plates. In still another example, the processor generates a data signal which corresponds to the flow stream positions of the positive particles, the negative particles and the neutral particles.

Based on the determined spatial positions of each flow stream, the processor automatically adjusts one or more parameters of the flow cytometer. For instance, the data signal may be used to adjust the position of a support stage having containers for collecting the positive particles, the negative particles and the neutral particles. In these instances, the processor generates a data signal corresponding to the spatial positions of each flow stream (i.e., neutral particle stream, positive particle stream and negative particle stream) and automatically adjusts the position of the support stage to align collection containers with each of the flow streams so as to optimize collection. For example, the position of the support stage may be automatically adjusted to align collection containers with each flow stream so that the number of particles collected by the containers is increased by 5% or more as compared to a container on a support structure not adjusted in response to the data signal, such as by 10% or more, such as 15% or more, such as 20% or more, such as 25% or more, such as 35% or more, such as 50% or more, such as 75% or more, such as 90% or more, such as 95% or more and including by 99% or more.

As summarized above, systems according to embodiments of the present disclosure include one or more processors that are automated to adjust parameters of a flow cytometer based on data signals derived from captured images of the flow cytometer flow stream. In certain embodiments, parameters of the flow cytometer which may be adjusted include sheath fluid pressure, hydrostatic pressure, droplet charging voltage, deflection plate voltage, charge correction value, drop delay, drop drive frequency, drop amplitude and charge phase.

In some embodiments, the processor may be configured to adjust the hydrostatic pressure in response to a data signal corresponding to one or more properties of the flow stream determined based on the captured images. In some instances, the hydrostatic pressure may be increased such as by 0.1 psi or more, such as 0.5 psi or more, such as by 1 psi or more, such as by 5 psi or more, such as by 10 psi or more, such as by 25 psi or more, such as by 50 psi or more, such as by 75 psi or more and including increasing the hydrostatic pressure by 100 psi or more. For example, the hydrostatic pressure may be increased by 1% or more, such as by 5% or more, such as by 10% or more, such as by 15% or more, such as by 25% or more, such as by 50% or more, such as by 75% or more and including by increasing the hydrostatic pressure by 90% or more. In other instances, the hydrostatic pressure is reduced, such as by 0.1 psi or more, such as 0.5 psi or more, such as by 1 psi or more, such as by 5 psi or more, such as by 10 psi or more, such as by 25 psi or more, such as by 50 psi or more, such as by 75 psi or more and including reducing the hydrostatic pressure by 100 psi or more. For example, the hydrostatic pressure may be reduced by 1% or more, such as by 5% or more, such as by 10% or more, such as by 15% or more, such as by 25% or more, such as by 50% or more, such as by 75% or more and including reducing the hydrostatic pressure by 90% or more.

In yet other embodiments, the processor may be configured to adjust the drop charging voltage in response to a data signal corresponding to one or more properties of the flow stream determined based on the captured images. In some instances, the drop charging voltage is increased, such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including increasing the drop charging voltage by 75V or more. For example, the drop charging voltage may be increased by 1% or more, such as by 5% or more, such as by 10% or more, such as by 15% or more, such as by 25% or more, such as by 50% or more, such as by 75% or more and including increasing the drop charging voltage by 90% or more. In other instances, the drop charging voltage is reduced, such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including reducing the drop charging voltage by 75V or more. For example, the drop charging voltage may be reduced by 1% or more, such as by 5% or more, such as by 10% or more, such as by 15% or more, such as by 25% or more, such as by 50% or more, such as by 75% or more and including reducing the drop charging voltage by 90% or more.

In yet other embodiments, the processor may be configured to adjust the deflection plate voltage in response to a data signal corresponding to one or more properties of the flow stream determined based on the captured images. In some instances, the deflection plate voltage is increased, such as by 5V or more, such as by 10V or more, such as by 50V or more, such as by 100V or more, such as by 250V or more, such as by 500V or more, such as by 1000V or more and including increasing the drop charging voltage by 2000V or more. For example, the deflection plate voltage may be increased by 1% or more, such as by 5% or more, such as by 10% or more, such as by 15% or more, such as by 25% or more, such as by 50% or more, such as by 75% or more and including increasing the deflection plate voltage by 90% or more. In other instances, the drop charging voltage is reduced, such as by 0.5V or more, such as by 5V or more, such as by 10V or more, such as by 50V or more, such as by 100V or more, such as by 250V or more, such as by 500V or more, such as by 1000V or more and including reducing the deflection plate voltage by 2000V or more. For example, the deflection plate voltage may be reduced by 1% or more, such as by 5% or more, such as by 10% or more, such as by 15% or more, such as by 25% or more, such as by 50% or more, such as by 75% or more and including reducing the deflection plate voltage by 90% or more.

In still other embodiments, the processor may be configured to adjust the drop drive frequency in response to a data signal corresponding to one or more properties of the flow stream determined based on the captured images. In some instances, the drop drive frequency is increased, such as by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more. For example, the drop drive frequency may be increased by 1% or more, such as by 5% or more, such as by 10% or more, such as by 15% or more, such as by 25% or more, such as by 50% or more, such as by 75% or more and including increasing the drop drive frequency by 90% or more. In other instances, the drop drive frequency is reduced, such as by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more. For example, the drop drive frequency may be reduced by 1% or more, such as by 5% or more, such as by 10% or more, such as by 15% or more, such as by 25% or more, such as by 50% or more, such as by 75% or more and including reducing the drop frequency by 90% or more. In still other embodiments, the processor may be configured to adjust the drop delay in response to a data signal corresponding to one or more properties of the flow stream determined based on the captured images. In some instances, the drop delay is increased, such as by 0.01 microseconds or more, such as by 0.05 microseconds or more, such as by 0.1 microseconds or more, such as by 0.3 microseconds or more, such as by 0.5 microseconds or more, such as by 1 microseconds or more, such as by 2.5 microseconds or more, such as by 5 microseconds or more, such as by 7.5 microseconds or more and including increasing the drop delay by 10 microseconds or more. For example, the drop delay may be increased by 1% or more, such as by 5% or more, such as by 10% or more, such as by 15% or more, such as by 25% or more, such as by 50% or more, such as by 75% or more and including increasing the drop delay by 90% or more. In other instances, the drop frequency is reduced, such as by 0.01 microseconds or more, such as by 0.05 microseconds or more, such as by 0.1 microseconds or more, such as by 0.3 microseconds or more, such as by 0.5 microseconds or more, such as by 1 microseconds or more, such as by 2.5 microseconds or more, such as by 5 microseconds or more, such as by 7.5 microseconds or more and including reducing the drop delay by 10 microseconds or more. For example, the drop delay may be reduced by 1% or more, such as by 5% or more, such as by 10% or more, such as by 15% or more, such as by 25% or more, such as by 50% or more, such as by 75% or more and including reducing the drop delay by 90% or more.

In still other embodiments, the processor may be configured to adjust the drop amplitude in response to a data signal corresponding to one or more properties of the flow stream determined based on the captured images. In some instances, the drop amplitude is increased, such as by 0.01 volts or more, such as by 0.025 volts or more, such as by 0.05 volts or more, such as by 0.1 volts or more, such as by 0.25 volts or more, such as by 0.5 volts or more and including increasing the drop amplitude by 1 volt or more. For example, the drop amplitude may be increased by 1% or more, such as by 5% or more, such as by 10% or more, such as by 15% or more, such as by 25% or more, such as by 50% or more, such as by 75% or more and including increasing the drop amplitude by 90% or more. In other instances, the drop amplitude is reduced, such as by 0.01 volts or more, such as by 0.025 volts or more, such as by 0.05 volts or more, such as by 0.075 volts or more, such as by 0.1 volts or more, such as by 0.25 volts or more and including reducing the drop amplitude by 1 volt or more. For example, the drop amplitude may be reduced by 1% or more, such as by 5% or more, such as by 10% or more, such as by 15% or more, such as by 25% or more, such as by 50% or more, such as by 75% or more and including reducing the drop amplitude by 90% or more.

In some embodiments, the processor is operably coupled to an imaging sensor which captures images of a flow cytometer flow stream in a detection field and generates a data signal corresponding to the physical dimensions of the flow stream based on the captured images. Where the flow stream is a continuous stream, in some instances the processor is configured to take the captured images and generate a data signal corresponding to the width of the flow stream. In detection fields where the flow stream is composed of discrete droplets, in some instances the processor is configured to generate a data signal corresponding to droplet diameter.

In certain embodiments, the processor may be configured to compare the physical dimensions of the flow stream determined from the captured images with dimensions expected based on empirical characteristics of the flow cytometer (such as flow cell nozzle orifice size and sheath fluid pressure) and inputted parameters by the user. In these embodiments, the processor is configured to generate a data signal corresponding to the ratio of the physical dimensions of the flow stream as compared to the expected flow stream dimensions based on the empirical characteristics of the flow cytometer and user inputted parameters. For example, the processor may be configured to generate a data signal which indicates that the flow stream is 99% or less of the expected size of the flow stream based on the empirical characteristics of the flow cytometer and user inputted parameters, such as 95% or less, such as 90% or less, such as 85% or less, such as 80% or less, such as 75% or less, such as 50% or less, such as 25% or less and including 10% or less of the expected size of the flow stream. In other embodiments, the processor may be configured to generate a data signal which indicates that the flow stream is greater than the size expected based on the empirical characteristics of the flow cytometer and user inputted parameters, such as being 105% or greater of the size of the flow stream, such a 110% or greater, such as 125% or greater and including 150% or greater. In these embodiments, the processor may be configured to automate adjustments to one or more parameters of the flow cytometer based on the data signal corresponding to the ratio of the flow stream size from the captured images and the expected size of the flow stream based on empirical characteristics of the flow cytometer and user input. For example, the processor may be configured to automatically adjust the pump rate, the hydrostatic pressure and drop drive frequency in response to the determined ratio.

In certain instances, the processor is configured for determining a flow cell nozzle opening diameter. In these embodiments, the processor is operably coupled to an imaging sensor which captures images of the flow stream at the orifice of the flow cell nozzle and generates a data signal corresponding to the physical dimensions of the flow stream. Based on the data signal corresponding to the physical dimensions of the flow stream, the processor is configured to determine the flow cell nozzle opening diameter. In some instances, based on the data signal corresponding to the physical dimensions of the flow stream the processor may determine that the flow cell nozzle opening diameter is 25 µm or greater, such as 35 µm or greater, such as 45 µm or greater, such as 50 µm or greater, such as 60 µm or greater, such as 75 µm or greater, such as 100 µm or greater and including 150 µm or greater. For example, the system may be configured to determine a flow cell nozzle opening diameter from the physical dimensions of the flow stream that ranges from 25 µm to 200 µm, such as from 35 µm to 175 µm, such as from 50 µm to 150 µm and including from 75 µm to 100 µm.

In certain instances, the nozzle opening diameter is determined based on the width of the flow stream. In other instances, the nozzle opening diameter is determined based on droplet volume.

The processor may, in certain instances, be configured to automatically adjust one or more parameters based on the determined nozzle opening diameter, such as for example, the hydrostatic pressure, the sheath fluid pressure, drop charge, deflection voltage, charge correction value, drop delay, drop drive frequency, drop amplitude charge phase and any combinations thereof, as discussed above.

In some embodiments, the processor may be configured to automatically adjust the drop drive frequency in response to the data signal corresponding to the flow cell nozzle orifice size determined using the captured images of the flow stream. For example, the drop drive frequency may be increased by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more. In other instances, the processor is configured to automatically reduce the drop drive frequency in response to the flow cell nozzle orifice size determined using the captured images of the flow stream, such as by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more.

In other embodiments, the processor may be configured to automatically adjust the sheath fluid pressure in response to the data signal corresponding to the flow cell nozzle orifice size determined using the captured images of the flow stream. For example, the sheath fluid pressure may be increased by 0.001 psi or more, such as 0.005 psi or more, such as by 0.01 psi or more, such as by 0.05 psi or more, such as by 0.1 psi or more, such as 0.5 psi or more, such as by 1 psi or more, such as by 5 psi or more, such as by 10 psi or more, such as by 25 psi or more, such as by 50 psi or more, such as by 75 psi or more and including increasing the sheath fluid pressure by 100 psi or more. In other instances, the processor is configured to automatically reduce the sheath fluid pressure in response to the flow cell nozzle orifice size determined using the captured images of the flow stream, such as by 0.1 psi or more, such as 0.5 psi or more, such as by 1 psi or more, such as by 5 psi or more, such as by 10 psi or more, such as by 25 psi or more, such as by 50 psi or more, such as by 75 psi or more and including reducing the sheath fluid pressure by 100 psi or more.

In some embodiments, systems of interest include an imaging sensor configured to capture images in a detection field at the break-off point of the flow stream. The term "break-off point" is used herein in its conventional sense to refer to the point at which the continuous flow stream begins to form droplets. In these embodiments, the subject systems include a processor operably coupled to the imaging sensor and configured to generate a data signal corresponding to the drop volume of droplets downstream from the break-off point. The processor takes the captured images of the flow stream droplets and measures the drop volume. The data signal corresponding to the drop volume may be used by the processor to automatically adjust one or more parameters of the flow cytometer.

In some embodiments, the data signal corresponding to drop volume is used by the processor to automatically adjust the drop drive frequency of the flow stream. For example, the processor may be configured to automatically reduce the drop drive frequency, such as by 5% or more, such as by 10% or more, such as by 15% or more, such as by 25% or more, such as by 50% or more, such as by 75% or more, such as by 90% or more, such as by 95% or more and including by 99% or more. In other instances, the processor is configured to automatically reduce the drop drive frequency by 2-fold or more in response to the data signal corresponding to the determined drop volume, such as by 3-fold or more, such as by 4-fold or more, such as by 5-fold or more and including by 10-fold or more. In yet other instances, the processor is configured to automatically increase the drop drive frequency, such as by 5% or more in response to the data signal corresponding to drop volume, such as by 10% or more, such as by 15% or more, such as by 25% or more, such as by 50% or more, such as by 75% or more, such as by 90% or more, such as by 95% or more and including by 99% or more. In still other instances, the processor is configured to automatically increase the drop drive frequency by 2-fold or more, such as by 3-fold or more, such as by 4-fold or more, such as by 5-fold or more and including by 10-fold or more.

In other embodiments, the data signal corresponding to the drop volume is used by the processor to automate sample collection volume during cell sorting. For example, the volume desired for each collected sample may be input into the processor and based on the data signal corresponding to the drop volume, the flow cytometer may be automated to stop collection of the sample after a predetermined amount of time, such as by removing the collection container or by ceasing the flow stream by the flow cytometer.

In some embodiments, the processor may be configured to determine the presence or absence of a flow stream in a detection field. Systems of interest may include an imaging sensor configured to capture images of the flow cytometer flow stream exiting the orifice of the flow cell nozzle and a processor operably coupled to the imaging sensor configured to assess the captured images to determine whether a flow stream is present or not present in the detection field. For example, determining whether a flow stream is present or not present in captured images of the flow cell nozzle orifice may be used to determine whether the flow cell has a clogged nozzle. In these embodiments, captured images by the imaging sensors are assessed by the processor and if a flow stream is detected in the images by the processor, the processor is configured to generate a signal indicating the presence of a flow stream. On the other hand, if after assessing the captured images, the processor determines that the flow stream is absent in the captured images, the processor may be configured to generate a signal indicating the absence of a flow stream.

Where the processor determines that no flow stream is present in the captured images, in certain embodiments, the subject systems are configured to automatically alert a user that the absence of flow stream is a result of flow cytometer malfunction, such as a clogged nozzle. In these embodiments, the processor correlates the data signal corresponding to the absence of a flow stream with input from the user as to whether a flow stream should be expected. In some embodiments, a user may configure the system to have a "closed loop" configuration where flow stream from the nozzle is directed to a waste receptacle without forming a flow stream. In these embodiments, the flow cytometer does not alert the user of a malfunction (e.g., clogged nozzle) since a flow stream is not expected. However, where a flow stream is expected (such as during normal use), the processor is automated to alert the user of a malfunction if after assessing the captured images no flow stream is detected.

In certain embodiments, after the processor has generated a data signal corresponding to one or more properties of the flow stream based on the captured images, an output module may communicate the parameters of the flow cytometer may be adjusted in response to the data signal. In some instances, the output module communicates an output in conjunction with the subject systems adjusting parameters of the flow cytometer. In other instances, the output module communicates the parameters before adjustment and may require confirmation of adjustment by the user. Output from the processor may be communicated to the user by any convenient protocol, such as for example by displaying on a monitor or by printing a report.

As discussed above, systems in some embodiments include one or more support stages operably coupled to the processors. Suitable support stages may be any convenient mounting device configured to hold in place one or more components of the subject systems, such as planar substrate, contoured mounting devices, cylindrical or tubular support structures, laser or LED holders, among other types of support structures. In some instances, the support stage is a mount for an illumination device, such as a laser or an LED. In other instances, systems include a support structure for holding one or more containers for collecting particles from the flow stream. For example, the support stage may be configured to hold in place containers including, but are not limited to test tubes, conical tubes, multi-compartment containers such as microtiter plates (e.g., 96-well plates), centrifuge tubes, culture tubes, microtubes, caps, cuvettes, bottles, rectilinear polymeric containers, among other types of containers.

Systems of interest may include one or more support stages, as desired, such as two or more, such as three or more, such as four or more and including five or more support stages. For example, the number of support stages may range from 1 to 10 support stages, such as from 2 to 7 support stages and including from 3 to 5 support stages. In certain embodiments, systems of interest include one support stage. In other embodiments, systems include two support stages. In one example, the subject systems include a support stage having a container for collecting droplets from the flow stream. In another example, the subject systems include a support stage having a mounted laser. In yet another example, the subject system includes a first support stage having a mounted laser and a second support stage having a container for collecting droplets from the flow stream.

In some embodiments, support stages are movable. For instance, in one example the support stage may be moved to adjust the position collection containers on the support stage so that they are aligned with the flow stream. In another example, the support stage may be moved to adjust the position of a laser. In some instances, the support stage is moved in two dimensions, such as in an X-Y plane orthogonal to the axis of the flow stream. In other instances, the support structure is moved in three dimensions. Where the support stage is configured to move, the support stage may be moved continuously or in discrete intervals. In some embodiments, the support stage is moved in a continuous motion. In other embodiments, the support stage is moved in discrete intervals, such as for example in 0.01 micron or greater increments, such as 0.05 micron or greater, such as 0.1 micron or greater, such as 0.5 micron or greater, such as 1 micron or greater, such as 10 micron or greater, such as 100 microns or greater, such as 500 microns or greater, such as 1 mm or greater, such as 5 mm or greater, such as 10 mm or greater and including 25 mm or greater increments.

Any displacement protocol may be employed to move the support structures, such as moving the support stages with a motor actuated translation stage, leadscrew translation assembly, geared translation device, such as those employing a stepper motor, servo motor, brushless electric motor, brushed DC motor, micro-step drive motor, high resolution stepper motor, among other types of motors.

Certain embodiments of the present disclosure may be described with reference to FIG. 1. A flow cytometer 100 employing an embodiment of the present invention is illustrated in FIG. 1. As discussed above, the flow cytometer 100 includes flow cell 104, a sample reservoir 106 for providing a fluid sample, (e.g., blood sample), to the flow cell and a sheath reservoir 108 for providing a sheath fluid to the flow cell. Flow cytometer 100 is configured to transport fluid sample having cells in a flow stream to flow cell 104 in conjunction with a laminating flow of sheath fluid. Analysis of the flow stream at an interrogation zone 103 within flow cell 104 may be used to determine properties of a sample and control the sorting parameters (as described herein). Sample interrogation protocols may include a source of light (e.g., laser) 112 for illuminating the flow stream and one or more detectors 109 (e.g., photomultiplier tubes (PMTs), charged coupled device (CCD)) or any other suitable type of light detecting device. Where light from the light source intersects the sample stream in interrogation zone 103, the laser light is scattered by the sample stream fluid and, in particular, by any cells present in the sample stream. A first portion of the scattered laser light will propagate in the direction prior to intersecting the sample stream (referred to herein as the forward scatter light). A second portion of the laser light intersecting the interrogation point will be scattered at an angle different from the direction of propagation (referred to herein as side scatter light). Within the flow cell 104, the sheath fluid surrounds the cell stream, and the combined sheath fluid and cell stream exits the flow cell 104 through a nozzle 102 having orifice 110 as flow stream 111. The flow stream may be continuous flow of fluid or a series of droplets depending on the action of a droplet generator.

The flow stream 111 exits the nozzle 102 at the nozzle orifice 110 which may have any diameter for example, 50 µm, 70 µm, 100 µm, or any other suitable diameter. The nozzle diameter will affect the properties of a flow stream, such as the stream dimensions, droplet break-off point and drop volume. To view the flow stream 111, a light source 112, such as an LED strobe, laser or any other illumination device, may optionally utilized and be positioned in the region of the sample fluid stream 111. A camera 113 or other image collection device may be positioned to capture an image of the flow stream in a first detection field. In some embodiments the flow stream may comprise a continuous stream or a series of droplets. If the flow stream is a continuous flow of liquid, the image captured by the camera in the detection field may provide a user or controller with sufficient information to determine the position and/or dimensions of the flow stream.

In some aspects of this invention the camera 113 or other detection device may affect some action in the flow cytometer 100 based on the image collected by the camera 113. A set-up controller 114 comprising a computer algorithm may receive the image of the flow stream and determine some action to be performed by the flow cytometer, advantageously freeing the user from manual set-up tasks. In some embodiments the diameter of the nozzle opening 110 may be determined based on an image analysis of the dimensions of the flow stream 111 captured by the camera 113. In some embodiments a set-up controller 114 may be operationally connected to the flow cytometer 100 and automatically initiate the adjustment of a series of parameters in the flow cytometer based upon the nozzle diameter determined from the image received by the camera. The parameters may include any flow cytometric parameter such as hydrostatic pressure, drop charge, deflection voltage, charge correction value, drop delay, drop frequency, drop amplitude, and charge phase.

The set-up controller 114 may be operationally connected to a fluidic system 115 that may control the rate of the flow stream 111 in the flow cytometer 100. The set-up controller 114 may initiate a pause in the flow stream based on an image received from the camera 113.

The image collected from the camera 113 of the flow stream 111 in the detection field may provide additional information about the position of the flow stream in an XY plane. The camera may be operationally connected to one or more stages 116, 119 and the position of the stage or stages may be moved in response to a signal from the camera or set-up controller connected to the camera. A collection device or light emitting device such as a laser 117 may be fixed to a stage and be beneficially aligned to intercept the flow stream 111 in response to the image from the camera 113. The light emitting device may be aligned to maximize the amount of light received by the flow stream. A collection device 118 may fixed to the first stage or to a second stage 119 and be aligned to maximize the collection of a flow stream or orient the flow stream with respect to a 'home position' on the collection device. The improved automatic alignment of the laser or collection device with the flow stream beneficially reduces the manual adjustment of the stage by the user.

A second camera 120 or data collection device may be positioned below the first camera 113 or data collection device and configured to collect an image in a second detection field. The second camera may be positioned orthogonally in an XY plane relative to the first camera, or optionally a series of optics may be positioned in an XY plane such that the first and second detection fields are orthogonally oriented. The second camera 120 may also be operationally connected to one or more moveable stages 116, 119 either directly or via the set-up controller 114. Collection or analysis devices may be fixed to the stages. The second detection field may be orthogonally oriented relative to the first detection field. Images from the second camera may be used to refine the flow stream position determined from the first camera and provide for improved positioning of one or more stages associated with the flow stream. Although cameras 113 and 120 are shown as individual detectors for exemplary purposes, a plurality of cameras can be used to detect the flow stream in a plurality of detection fields. An additional light source 123 may be utilized to provide sufficient illumination to capture the image of the flow stream at this position. Alternatively the laser 117 may provide sufficient illumination. Furthermore, filters or other optics 121 and 122 may be positioned in front of the light receiving areas of cameras 113 and 120, respectively, to filter out any light or to adjust the resolution or direction of the detection field.

The images from the first and/or second camera 113, 120 may be analyzed by a set-up controller 114 to determine any number of properties of the flow stream, such as position of the flow stream in a detection field or dimensions of the flow stream. In some embodiments a signal corresponding to the location of the flow stream in the detection field may be transmitted to a set-up controller 114 or directly to a movable stage 116, 119 and initiate the automatic alignment of devices or vessels fixed to the stage with respect to the flow stream.

The flow stream may be a series of droplets that are partially deflected by a pair of deflection plates 124 and become a plurality of streams 125, 126, 127. As further illustrated, the flow cytometer may include a plurality of collection vessels 118, 128 and 129 to collect the plurality of flow streams. The collection vessels may be a single vessel with a multiple wells such as a 96 or 364 well plate or a series of vessels. In the example shown in FIG. 1, droplets 127 that have been negatively charged in the interrogation zone will be directed by the potentials applied to the deflection plates 124 toward collection vessel 128. Droplets 126 which have been neither positively nor negatively charged will not be deflected by the potentials applied to deflection plates 124, and therefore continue along their original path into central collection vessel 118. Droplets 125 which have been positively charged will be deflected by the potentials applied to deflection plates 124 toward collection vessel 129. Alignment of the collection vessels with respect to deflected flow streams is essential to maximizing collections of sorted cells.

The collection vessel or vessels may be automatically aligned by collecting data from the first and or second camera 113, 120 to determine the position of the flow streams in an XY plane. The collection vessel(s) may be fixed to a movable stage 119 in communication with the controller 114 or directly with the first or second camera 113, 120. The cameras may determine the position of the stream in the detection field, and generate a signal to the controller. The controller 114 may automatically control the position of a collection vessel 118 disposed beneath the flow stream in order to optimize the position of the collection vessel with respect to the flow stream. In some embodiments the controller may also control the magnitude of the electric charge received by a portion of the droplets. The magnitude of the electric charge may affect the degree of deflection experienced by the droplets and hence the position of the droplets in the XY plane.

The set-up controller 118 may take further action depending parameters input in the device. One aspect of the invention is the application of an input value for drop-volume into the set-up controller 114. The drop volume may be determined by any means such as empirical measurements of a volume after a set number of drops from a particular nozzle diameter have been collected in a defined period of time. The drop volume may then be input into the set-up controller 114. In some embodiments the controller may cause the fluidics system 115 to pause after a set volume is dispensed to a collection vessel 118. This method beneficially improves a collection protocol because the use of a calibrated drop volume may provide a more accurate determination of collection volume than conventional methods which rely on drop count to control collection times. Using methods of this invention and the sorted fluid volume information available, an additional "stopping rule" for the sorting process may be implemented.

In some aspects of this invention, the set-up controller may be used to distinguish between a clogged nozzle and a closed loop nozzle specifically designed not to generate a flow stream. The "closed loop" nozzle has an output that is connected to a tubing system that goes directly to waste. It does not create an open, sortable stream, and is used for analysis only. It is important to be able to discern this nozzle from a clogged sorting nozzle that should create an open, sortable stream but is unable for whatever reason. In some embodiments the set-up controller electrically senses when the closed loop nozzle is installed. The electrical sensing may take any form such as an inserted closed loop nozzle providing a ground to a 'pull up' resistor circuit. If the closed loop nozzle is sensed in this way, an image of a stream is not expected by the camera, so a clogged nozzle is not erroneously reported when a stream image is not seen. For sorting nozzles, a stream image is expected, and using the area value of that image, a nozzle size is determined the appropriate instrument setting values for the nozzle are executed. If a stream image is not seen and an electrical signal signifying the presence of a closed loop nozzle is not detected, it is determined a sorting nozzle is installed and clogged. The set-up controller may initiate a series of actions in this event. For example, the user may be notified of a clogged nozzle, the fluidic system may be paused, or any other action may be initiated.

Methods for Adjusting Parameters of a Flow Cytometer

Aspects of the disclosure also include methods for adjusting one or more parameters of a flow cytometer. Methods according to certain embodiments include capturing one or more images of a flow stream of the flow cytometer in a detection field, determining one or more properties of the flow stream in the detection field, generating a data signal corresponding to the one or more properties of the flow stream and adjusting one or more parameters of the flow cytometer in response to the data signal.

As discussed above, the term "adjusting" refers to changing one or more functional parameters of the flow cytometer. The desired adjustment may vary in terms of goal, where in some instances the desired adjustments are adjustments that ultimately result in enhanced efficiency of some desirable parameter, e.g., improved cell sorting accuracy, enhanced particle collection, identifying component malfunction (e.g., clogged flow cell nozzle), energy consumption, particle charging efficiency, more accurate particle charging, enhanced particle deflection during cell sorting, among other adjustments. In embodiments, the subject methods reduce or entirely eliminate the need for user input or manual adjustment during sample analysis with a flow cytometer. In certain embodiments, methods of interest may be fully automated, such that adjustments made in response to data signals corresponding to one or more parameters of the flow stream require little to no human intervention or manual input by the user. In certain embodiments, methods include adjusting one or more parameters of the flow cytometer based on the data signals corresponding to one or more parameters of the flow stream without any human intervention, such as two or more parameters, such as three or more parameters, such as four or more parameters and including five or more parameters. In some embodiments, methods may include adjusting the hydrostatic pressure, the sheath fluid pressure, drop charge, deflection voltage, charge correction value, drop delay, drop drive frequency, drop amplitude charge phase and any combinations thereof.

In practicing methods according to certain embodiments, one or more images of a flow cytometer flow stream are captured in a detection field. As discussed above, the detection fields may vary depending on the properties of the flow stream being interrogated. In embodiments, methods may include capturing in an image a detection field that spans 0.001 mm or more of the flow stream, such as 0.005 mm or more, such as 0.01 mm or more, such as 0.05 mm or more, such as 0.1 mm or more, such as 0.5 mm or more, such as 1 mm or more, such as 2 mm or more, such as 5 mm or more and including 10 mm or more of the flow stream. The detection field interrogated may vary. In some embodiments, the detection field includes the flow cell nozzle orifice. In other embodiments, the detection field includes the location of the flow stream where the drops containing the particles of interest are charged (i.e., the "break-off" point where the continuous flow stream begins to form discrete droplets). In yet other embodiments, the detection field includes the region where charged particles are deflected by deflector plates during cell sorting.

In capturing one or more images of the flow stream, a detection field is illuminated with a light source. In some embodiments, the flow stream is illuminated with a broadband light source or with a narrow band of light (as described above). Suitable broadband light source protocol may include, but are not limited to a halogen lamp, deuterium arc lamp, xenon arc lamp, stabilized fiber-coupled broadband light source, a broadband LED with continuous spectrum, superluminescent emitting diode, semiconductor light emitting diode, wide spectrum LED white light source, an multi-LED integrated white light source, among other broadband light sources or any combination thereof. Suitable narrow band light sources, include but are not limited to a narrow wavelength LED, laser diode or a broadband light source coupled to one or more optical bandpass filters, diffraction gratings, monochromators or any combination thereof.

In certain embodiments, the light source is a stroboscopic light source where the flow stream is illuminated with periodic flashes of light. For example, the frequency of light strobe may be 0.01 kHz or greater, such as 0.05 kHz or greater, such as 0.1 kHz or greater, such as 0.5 kHz or greater, such as 1 kHz or greater, such as 2.5 kHz or greater, such as 5 kHz or greater, such as 10 kHz or greater, such as 25 kHz or greater, such as 50 kHz or greater and including 100 kHz or greater. In some instances, the strobe frequency is synchronized with droplet drive frequency. In other instances, the strobe frequency is synchronized with image capture.

Capturing one or more images of the flow stream may include illuminating the flow stream with a combination of light sources, such as with two or more light sources, such as three or more light sources, such as four or more light sources and including five or more light sources. Where more than one light source is employed, the flow stream may be illuminated with the light sources simultaneously or sequentially, or a combination thereof. For example, where images of the flow stream are captured by illuminating with two light sources, the subject methods may include simultaneously illuminating the flow stream with both light sources. In other embodiments, capturing images of the flow stream may include sequentially illuminating with two light sources. Where two light sources are illuminated sequentially, the time each light source illuminates the flow stream may independently be 0.001 seconds or more, such as 0.01 seconds or more, such as 0.1 seconds or more, such as 1 second or more, such as 5 seconds or more, such as 10 seconds or more, such as 30 seconds or more and including 60 seconds or more. In embodiments where images of the flow stream are captured by sequentially illuminating with two or more light sources, the duration the flow stream is illuminated by each light source may be the same or different.

Images of the flow stream may be captured continuously or in discrete intervals. In some instances, methods include capturing images continuously. In other instances, methods include capturing images in discrete intervals, such as capturing an image of the flow stream every 0.001 millisecond, every 0.01 millisecond, every 0.1 millisecond, every 1 millisecond, every 10 milliseconds, every 100 milliseconds and including every 1000 milliseconds, or some other interval.

One or more images may be captured in each detection field, such as 2 or more images of the flow stream in each detection field, such as 3 or more images, such as 4 or more images, such as 5 or more images, such as 10 or more images, such as 15 or more images and including 25 or more images. Where more than one image is captured in each detection field, the plurality of images may be automatically stitched together by a processor having digital image processing algorithm.

Images of the flow stream in each detection field may be captured at any suitable distance from the flow stream so long as a usable image of the flow stream is captured. For example, images in each detection field may captured at 0.01 mm or more from the flow stream, such as 0.05 mm or more, such as 0.1 mm or more, such as 0.5 mm or more, such as 1 mm or more, such as 2.5 mm or more, such as 5 mm or more, such as 10 mm or more, such as 15 mm or more, such as 25 mm or more and including 50 mm or more from the flow cytometer flow stream. Images of the flow stream in each detection field may also be captured at any angle from the flow stream. For example, images in each detection field may captured at an angle with respect to the axis of the flow stream which ranges from 10° to 90°, such as from 15° to 85°, such as from 20° to 80°, such as from 25° to 75° and including from 30° to 60°. In certain embodiments, images in each detection field may captured at a 90° angle with respect to the axis of the flow stream.

In some embodiments, capturing images of the flow stream include moving one or more imaging sensors alongside the path of the flow stream. For instance, the imaging sensor may be moved upstream or downstream alongside the flow stream capturing images in a plurality of detection fields. For example, methods may include capturing images of the flow stream in two or more different detection fields, such as 3 or more detection fields, such as 4 or more detection fields and including 5 or more detections fields. The imaging sensor may be moved continuously or in discrete intervals. In some embodiments, the imaging sensor is moved continuously. In other embodiments, the imaging sensor may be moved along the flow stream path in discrete intervals, such as for example in 1 mm or greater increments, such as 2 mm or greater increments and including 5 mm or greater increments.

As summarized above, methods include generating a data signal corresponding to one or more properties of the flow stream from the captured images. In detection fields where the flow stream is continuous, methods may include generating a data signal corresponding to the spatial position of the flow stream, the dimensions of the flow stream such as flow stream width, as well as flow rate and flow turbulence based on the captured images. In detection fields where the flow stream is composed of discrete droplets, methods may include generating a data signal corresponding to the spatial position of the flow stream, drop size including drop diameter and volume, drop drive frequency, drop amplitude as well as the uniformity of drop size and frequency. In certain embodiments, methods include generating a data signal corresponding to the ratio of the size of the flow stream as compared to the expected size of the flow stream based on empirical characteristics of the flow cytometer and user inputted data. In other embodiments, methods include assessing the captured images to determine whether a flow stream is present or absent in a particular detection field. In yet other embodiments, methods include assessing the captured images of the flow stream to determine the flow cell nozzle orifice size.

In some embodiments, methods include capturing one or more images of a flow stream of the flow cytometer in a detection field, determining the spatial position of the flow stream in the detection field based on the captured images and generating a data signal corresponding to the spatial position of the flow stream. For instance, methods may include capturing images of the flow stream in a detection field and mapping the spatial position of the flow stream in an X-Y plane. In some instances, the position of the flow stream in the X-Y plane is compared to the vertical axis of the flow cell nozzle to determine position of the flow stream with respect to the vertical axis formed by the flow cell nozzle. Where the spatial position of the flow stream is determined in more than one detection field, the spatial position of the flow stream may be mapped in an X-Y plane in each detection field and compared to fine tune the precise spatial position of the flow stream in the X-Y plane. Based on the determined spatial position of the flow stream in the detection field, methods may include generating a data signal corresponding to the spatial position of the flow stream.

In embodiments according to the subject methods, one or more parameters of the flow cytometer are adjusted in response to the data signal corresponding to the spatial position of the flow stream. In some instances, the data signal is used to adjust the position of a support stage having containers for collecting particles, such as during cell sorting. In certain embodiments, methods include generating a data signal corresponding to the spatial position of the flow stream and automatically adjusting the position of a support stage so that the collection containers on the support stage are aligned with the trajectory of the flow stream. For example, methods may include mapping the position of the flow stream in each detection field in an X-Y plane, mapping the position of the container in the X-Y plane and matching the position of the container in the X-Y plane with the position of the flow stream in the X-Y plane to align the collection container with the flow stream. In some instances, methods include mapping the position of the flow stream in two detection fields. In these instances, the spatial position of the flow stream is mapped in the first detection field in an X-Y plane and the spatial position of the flow stream is mapped in the second detection field in the X-Y plane. Based on the mapped positions of the flow stream in the first and second detection field, a data signal is generated corresponding to the spatial position of the flow stream in the flow cytometer.

In these embodiments, a data signal is generated corresponding to the spatial position of the flow stream and automatically adjusting the position of a support stage in an X-Y plane so as to optimize collection of the flow stream. For example, optimizing collection of the particles may include reducing the number of particles not collected by the containers on the support stage due to misalignment of the flow stream with the collection containers, such as by 5% or more as compared collecting the flow stream in a container on a support stage not adjusted in response to the data signal, such as by 10% or more, such as 15% or more, such as 20% or more, such as 25% or more, such as 35% or more, such as 50% or more, such as 75% or more, such as 90% or more, such as 95% or more and including by 99% or more.

As described above, support stages may be positioned anywhere along the flow stream as desired when collecting particles from the flow stream. In some instances, particles are collected into containers on a support stage positioned downstream from deflector plates where the flow stream droplets have been separated based on charge (e.g., positive, negative and neutral). In these instances, methods include capturing images of a flow stream in a detection field downstream from the deflector plates and generating a data signal corresponding to the spatial positions of the flow streams of the positive, negative and neutral particles. Based on the determined spatial positions of the flow streams from the captured images, the position of a support stage having a multi-compartment container (or three separate containers) may be automatically adjusted to optimize collection of each flow stream. For example, methods may include adjusting the position of the support stage such that collection of the flow streams is improved by 5% or more as compared collecting the flow streams on a support stage not adjusted in response to the data signal, such as by 10% or more, such as 15% or more, such as 20% or more, such as 25% or more, such as 35% or more, such as 50% or more, such as 75% or more, such as 90% or more, such as 95% or more and including by 99% or more.

Figure 2:
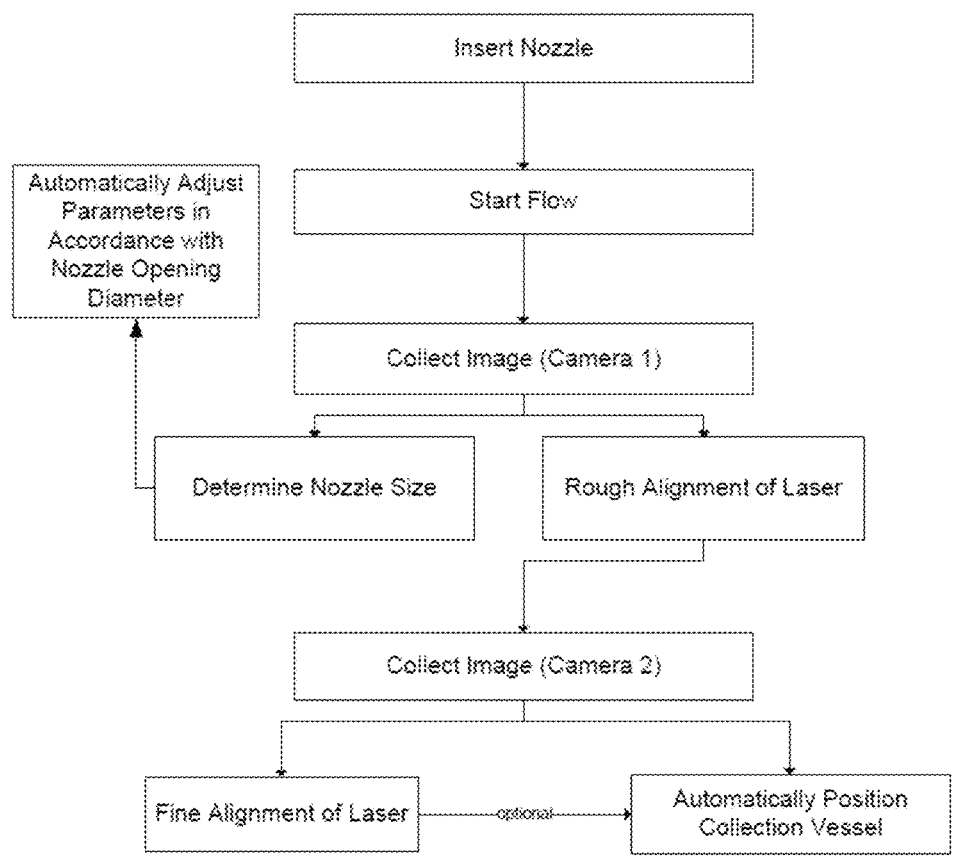
FIG. 2 depicts a flow chart illustrating steps for practicing methods of the present disclosure according to certain embodiments.

Methods according to certain embodiments are outlined in the combination of steps shown in FIG. 2. The steps of this invention may occur in any order or in any combination. For example in FIG. 2, an experimental set-up may include the installation of a nozzle appropriate for the sorting task desired. The flow stream may be initiated and an image collected of the flow stream by camera 1. The nozzle opening may be determined from the image of the flow stream and any number of parameters may be automatically determined and set based on this value. The laser may be automatically and roughly aligned in accordance with the signal from the first camera. As the flow stream flows past camera 2, a second image may be captured. The two images from camera 1 and camera 2 may provide for precise localization of the flow stream in an XY plane. A laser may be automatically and finely positioned based on this information and a collection vessel may be automatically positioned based on this information. In some embodiments the fine alignment of the laser may facilitate the alignment of the collection vessel.

As summarized above, methods according to embodiments of the present disclosure include adjusting one or more parameters of the flow cytometer in response to data signals derived from captured images in one or more detection fields of a flow cytometer flow stream. In certain embodiments, methods include adjusting sheath fluid pressure, droplet charging voltage, deflection plate voltage, charge correction value, drop delay, drop drive frequency, drop amplitude and charge phase or a combination thereof.

In some embodiments, methods including adjusting the sheath fluid pressure in response to a data signal corresponding to one or more properties of the flow stream determined based on the captured images. In some instances, the sheath fluid pressure may be increased such as by 0.001 psi or more, such as 0.005 psi or more, such as by 0.01 psi or more, such as by 0.05 psi or more, such as by 0.1 psi or more, such as 0.5 psi or more, such as by 1 psi or more, such as by 5 psi or more, such as by 10 psi or more, such as by 25 psi or more, such as by 50 psi or more, such as by 75 psi or more and including increasing the hydrostatic pressure by 100 psi or more. In other instances, the sheath fluid pressure is reduced, such as by 0.001 psi or more, such as 0.005 psi or more, such as by 0.01 psi or more, such as by 0.05 psi or more, such as by 0.1 psi or more, such as 0.5 psi or more, such as by 1 psi or more, such as by 5 psi or more, such as by 10 psi or more, such as by 25 psi or more, such as by 50 psi or more, such as by 75 psi or more and including reducing the hydrostatic pressure by 100 psi or more.

In yet other embodiments, methods include adjusting the drop charging voltage in response to a data signal corresponding to one or more properties of the flow stream determined based on the captured images. In some instances, the drop charging voltage is increased, such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including increasing the drop charging voltage by 75V or more. In other instances, the drop charging voltage is reduced, such as by 0.01 V or more, such as 0.05 V or more, such as 0.1 V or more, such as by 0.5V or more, such as by 1V or more, such as by 5V or more, such as by 10V or more, such as by 15V or more, such as by 25V or more, such as by 50V or more and including reducing the drop charging voltage by 75V or more.

In yet other embodiments, methods include adjusting the deflection plate voltage in response to a data signal corresponding to one or more properties of the flow stream determined based on the captured images. In some instances, the deflection plate voltage is increased, such as by 5V or more, such as by 10V or more, such as by 50V or more, such as by 100V or more, such as by 250V or more, such as by 500V or more, such as by 1000V or more and including increasing the deflection plate voltage by 2000V or more. In other instances, the drop charging voltage is reduced, such as by 5V or more, such as by 10V or more, such as by 50V or more, such as by 100V or more, such as by 250V or more, such as by 500V or more, such as by 1000V or more and including reducing the deflection plate voltage by 2000V or more.

In still other embodiments, methods include adjusting the drop drive frequency in response to a data signal corresponding to one or more properties of the flow stream determined based on the captured images. In some instances, the drop drive frequency is increased, such as by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more. In other instances, the drop frequency is reduced, such as by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more.

In still other embodiments, methods include adjusting the drop delay in response to a data signal corresponding to one or more properties of the flow stream determined based on the captured images. In some instances, the drop delay is increased, such as by 0.01 microseconds or more, such as by 0.05 microseconds or more, such as by 0.1 microseconds or more, such as by 0.3 microseconds or more, such as by 0.5 microseconds or more, such as by 1 microseconds or more, such as by 2.5 microseconds or more, such as by 5 microseconds or more, such as by 7.5 microseconds or more and including increasing the drop delay by 10 microseconds or more. In other instances, the drop frequency is reduced, such as by 0.01 microseconds or more, such as by 0.05 microseconds or more, such as by 0.1 microseconds or more, such as by 0.3 microseconds or more, such as by 0.5 microseconds or more, such as by 1 microseconds or more, such as by 2.5 microseconds or more, such as by 5 microseconds or more, such as by 7.5 microseconds or more and including reducing the drop delay by 10 microseconds or more.

In still other embodiments, methods include adjusting the drop amplitude in response to a data signal corresponding to one or more properties of the flow stream determined based on the captured images. In some instances, the drop amplitude is increased, such as by 0.01 volts or more, such as by 0.025 volts or more, such as by 0.05 volts or more, such as by 0.1 volts or more, such as by 0.25 volts or more, such as by 0.5 volts or more and including increasing the drop amplitude by 1 volt or more. In other instances, the drop amplitude is reduced, such as by 0.01 volts or more, such as by 0.025 volts or more, such as by 0.05 volts or more, such as by 0.075 volts or more, such as by 0.1 volts or more, such as by 0.25 volts or more and including reducing the drop amplitude by 1 volt or more.

In some embodiments, methods include capturing one or more images of a flow stream of the flow cytometer in a detection field, characterizing the physical dimensions of the flow stream in the detection field based on the captured images and generating a data signal corresponding to the physical dimensions of the flow stream. In detection fields where the flow stream is a continuous stream, methods may include taking the captured images and generating a data signal corresponding to the width of the flow stream. In detection fields where the flow stream is composed of discrete droplets, methods may include taking the captured images and generating data signals corresponding to droplet size, such as droplet diameter.

In certain instances, methods may include determining a flow cell nozzle orifice diameter based on the captured images. In these instances, methods may include capturing images of the flow stream at the orifice of the flow cell nozzle and generating a data signal corresponding to the physical dimensions of the flow stream. Based on the data signal corresponding to the physical dimensions of the flow stream, the flow cell nozzle opening diameter is determined. In certain instances, methods include determining the flow cell nozzle opening diameter using the width of the flow stream. In other instances, methods include determining the flow cell nozzle opening diameter using the droplet diameter. In these embodiments, methods may further include automating adjustments to one or more parameters of the flow cytometer based the determined flow cell nozzle opening diameter. For example, methods may include automatically adjusting the sheath fluid pressure, drop drive frequency, drop charge, deflection voltage, charge correction value, drop delay, drop frequency, drop amplitude charge phase and or a combination thereof, as discussed above.

In certain embodiments, methods may include automating adjustments to the drop drive frequency in response to the determined flow cell nozzle orifice diameter. For example, the drop drive frequency may be increased by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more. In other instances, methods include reducing the drop drive frequency in response to the determined flow cell nozzle orifice diameter, such as by 0.01 Hz or more, such as by 0.05 Hz or more, such as by 0.1 Hz or more, such as by 0.25 Hz or more, such as by 0.5 Hz or more, such as by 1 Hz or more, such as by 2.5 Hz or more, such as by 5 Hz or more, such as by 10 Hz or more and including by 25 Hz or more.

In other embodiments, methods may include automating adjustments to the sheath fluid pressure in response to the determined flow cell nozzle orifice diameter. For example, the sheath fluid pressure may be increased by 0.001 psi or more, such as 0.005 psi or more, such as by 0.01 psi or more, such as by 0.05 psi or more, such as by 0.1 psi or more, such as 0.5 psi or more, such as by 1 psi or more, such as by 5 psi or more, such as by 10 psi or more, such as by 25 psi or more, such as by 50 psi or more, such as by 75 psi or more and including increasing the sheath fluid pressure by 100 psi or more. In other instances, methods include reducing the sheath fluid pressure in response to the determined flow cell nozzle orifice diameter, such as by 0.001 psi or more, such as 0.005 psi or more, such as by 0.01 psi or more, such as by 0.05 psi or more, such as by 0.1 psi or more, such as 0.5 psi or more, such as by 1 psi or more, such as by 5 psi or more, such as by 10 psi or more, such as by 25 psi or more, such as by 50 psi or more, such as by 75 psi or more and including reducing the sheath fluid pressure by 100 psi or more.

In some embodiments, methods may include comparing the physical dimensions of the flow stream determined from the captured images with dimensions expected based on empirical characteristics of the flow cytometer (such as flow cell nozzle orifice size and sheath fluid pressure) as well as inputted parameters by the user. In these instances, methods include generating a data signal corresponding to the ratio of the physical dimensions of the flow stream determined from the captured images as compared to the expected flow stream dimensions based on the empirical characteristics of the flow cytometer and user inputted parameters. For example, methods may include generating a data signal which indicates that the flow stream as determined from the captured images is 99% or less of the expected size of the flow stream, such as 95% or less, such as 90% or less, such as 85% or less, such as 80% or less, such as 75% or less, such as 50% or less, such as 25% or less and including 10% or less of the expected size of the flow stream. In other embodiments, methods may include generating a data signal which indicates that the flow stream as determined from the captured images is greater than the size expected, such as being 105% or greater of the size of the flow stream, such a 110% or greater, such as 125% or greater and including 150% or greater. In these embodiments, methods may further include automating adjustments to one or more parameters of the flow cytometer based on the generated data signal. For example, methods may include automatically adjusting the sheath fluid pump rate, the sheath fluid pressure or drop drive frequency.

Methods of interest may also include capturing images in a detection field the break-off point of the flow stream, generating a data signal corresponding to drop volume of droplets downstream from the break-off point and adjusting one or more properties of the flow cytometer in response to the determined drop volume. In some embodiments, methods include automatically adjusting the drop drive frequency of the flow stream in response to the determined drop volume. For example, methods may include reducing the drop drive frequency, such as by 5% or more, such as by 10% or more, such as by 15% or more, such as by 25% or more, such as by 50% or more, such as by 75% or more, such as by 90% or more, such as by 95% or more and including by 99% or more. In other instances, methods may include increasing the drop drive frequency in response to the determined drop volume, such as by 5% or more, such as by 10% or more, such as by 15% or more, such as by 25% or more, such as by 50% or more, such as by 75% or more, such as by 90% or more, such as by 95% or more and including by 99% or more.

In other embodiments, methods include automatically regulating sample collection volume during cell sorting based on the determined drop volume. For example, the volume desired for each collected sample may be input into a processor and based on the data signal corresponding to the drop volume, the flow cytometer may be automated to stop collection of the sample after a predetermined amount of time, such as by removing the collection container or by ceasing the flow stream by the flow cytometer.

In yet other embodiments, methods may include capturing images of a flow stream in a detection field, determining the presence or absence of a flow stream in the detection field and adjusting one or more parameters of the flow cytometer in response to the determined presence or absence of the flow stream. As discussed above, the subject methods for determining whether a flow stream is present or not present in captured images of the flow cell nozzle orifice may be used to determine whether the flow cell has a clogged nozzle. In these embodiments, captured images by the imaging sensors are assessed and if a flow stream is detected in the images, a data signal is generated indicating the presence of a flow stream. On the other hand, if after assessing the captured images, it is determined that the flow stream is absent in the captured images, a data signal is generated indicating the absence of a flow stream.

Where no flow stream is present in the captured images, in certain embodiments, methods may include automatically alerting a user that the absence of flow stream is a result of flow cytometer malfunction, such as a clogged nozzle. In these embodiments, data signal corresponding to the absence of a flow stream is correlated with input from the user as to whether a flow stream should be expected. In some embodiments, where a user has configured the system to have a "closed loop" configuration, no flow stream is expected. In these embodiments, the flow cytometer does not alert the user of a malfunction (e.g., clogged nozzle) since a flow stream is not expected.

Figure 3:
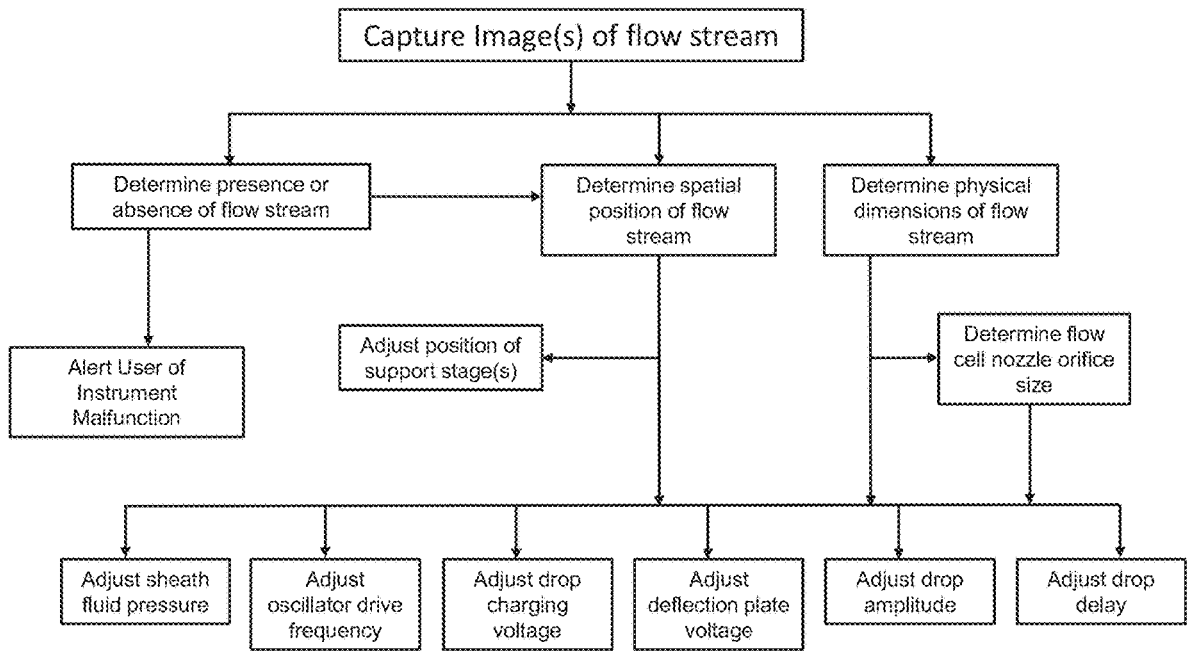
FIG. 3 depicts a flow chart illustrating steps for practicing methods of the present disclosure according to certain embodiments.

FIG. 3 depicts a flow chart illustrating methods for adjusting one or more parameters of a flow cytometer according to certain embodiments of the present disclosure. As summarized above, methods include capturing one or more images in a detection field of a flow cytometer flow stream. The images may, in certain instances, be captured in two or more detection fields, such as 3 or more and including 4 or more detection fields. In some embodiments, methods include determining whether a flow stream is present or absent. Where a flow stream is determined to be absent and a flow stream is expected (such as during normal usage), an alert may be conveyed to the user of a possible instrument malfunction (e.g., clogged nozzle). In other embodiments, methods include determining the spatial position of the flow stream or determining the physical dimensions of the flow stream. In certain instances, methods include initially determining that a flow stream is present in the one or more captured images, followed by determining the spatial position of the flow stream. In other instances, methods include initially determining that a flow stream is present in the one or more captured images, followed by determining the physical dimensions of the flow stream. In some embodiments, methods including determining a physical property of the flow cytometer based on the physical dimensions of the flow stream from the captured images. For example, the flow cell nozzle orifice may be determined based on the physical dimensions of the flow stream from the captured images.

Methods also include automatically adjusting one or more parameters of the flow cytometer in response to data signals derived from captured images, such as adjusting sheath fluid pressure, droplet charging voltage, deflection plate voltage, charge correction value, drop delay, drop drive frequency, drop amplitude and charge phase or a combination thereof. In certain embodiments, the one or more parameters includes adjusting the position of one or more support stages, for example, a support stage having a container for collecting flow stream particles during cell sorting.

As discussed above, the subject methods may be fully automated, such that adjustments are made in response to data signals corresponding to one or more parameters of the flow stream with little, if any, human intervention or manual input by the user.

Computer-Controlled Systems

Aspects of the present disclosure further include computer controlled systems for practicing the subject methods, where the systems further include one or more computers for complete automation or partial automation of a system for practicing methods described herein. In some embodiments, systems include a computer having a computer readable storage medium with a computer program stored thereon, where the computer program when loaded on the computer includes instructions for capturing one or more images of a flow stream of the flow cytometer in a detection field; algorithm for determining the spatial position of the flow stream in the detection field; algorithm for generating a data signal corresponding to the spatial position of the flow stream; and instructions for adjusting one or more parameters of the flow cytometer in response to the data signal. In certain instances, systems include a computer having a computer readable storage medium with a computer program stored thereon, where the computer program when loaded on the computer includes instructions for capturing one or more images of a flow stream of the flow cytometer in a detection field; algorithm for determining the physical dimensions of the flow stream in the detection field; algorithm for generating a data signal corresponding to the physical dimensions of the flow stream; and instructions for adjusting one or more parameters of the flow cytometer in response to the data signal.

In embodiments, the system includes an input module, a processing module and an output module. Processing modules of interest may include one or more processors that are configured and automated to adjust one or more parameters of a flow cytometer as described above. For example processing modules may include two or more processors that are configured and automated to adjust one or more parameters of a flow cytometer as described above, such as three or more processors, such as four or more processors and including five or more processors.

In some embodiments, the subject systems may include an input module such that parameters or information about the fluidic sample, sheath fluid pressure, hydrostatic pressure, flow stream charge, deflection voltage, charge correction value, drop delay, drop drive frequency, drop amplitude and charge phase, flow cell nozzle orifice, position of support stages, imaging sensors, light sources, optical adjustment protocols, amplifiers as well as properties, resolution and sensitivity of imaging sensors may be input before practicing the subject methods.

As described above, each processor includes memory having a plurality of instructions for performing the steps of the subject methods, such as capturing one or more images of a flow stream of the flow cytometer in a detection field; determining one or more properties of the flow stream in the detection field; generating a data signal corresponding to the one or more properties of the flow stream; and adjusting one or more parameters of the flow cytometer in response to the data signal. After the processor has performed one or more of the steps of the subject methods, the processor may be automated to make adjustments to parameters of the flow cytometer, such as adjustments as described above.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing the steps of the subject methods. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; portable flash drive; and hybrids of these categories such as magnetic/optical storage media.

The processor may also have access to a communication channel to communicate with a user at a remote location. By remote location is meant the user is not directly in contact with the system and relays input information to an input manager from an external device, such as a a computer connected to a Wide Area Network ("WAN"), telephone network, satellite network, or any other suitable communication channel, including a mobile telephone (i.e., smartphone).

In some embodiments, systems according to the present disclosure may be configured to include a communication interface. In some embodiments, the communication interface includes a receiver and/or transmitter for communicating with a network and/or another device. The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the subject systems and other external devices such as a computer terminal (for example, at a physician's office or in hospital environment) that is configured for similar complementary data communication.

In one embodiment, the communication interface is configured for infrared communication, Bluetooth® communication, or any other suitable wireless communication protocol to enable the subject systems to communicate with other devices such as computer terminals and/or networks, communication enabled mobile telephones, personal digital assistants, or any other communication devices which the user may use in conjunction.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the subject systems are configured to wirelessly communicate with a server device via the communication interface, e.g., using a common standard such as 802.11 or Bluetooth® RF protocol, or an IrDA infrared protocol. The server device may be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen.

In some embodiments, the communication interface is configured to automatically or semi-automatically communicate data stored in the subject systems, e.g., in an optional data storage unit, with a network or server device using one or more of the communication protocols and/or mechanisms described above.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g., over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Windows 8, iOS, Sun Solaris, Linux, OS/400, Compaq Tru64 Unix, SGI IRIX, Siemens Reliant Unix, and others.

Utility

The subject systems, methods, and computer systems find use in a variety of different applications where it is desirable to automate adjustments to one or more parameters of a flow cytometer to provide for fast, reliable systems for characterizing and sorting cells from a biological sample. Embodiments of the present disclosure find use where minimizing the amount of reliance on human input and adjustments to the system are desired, such as in research and high throughput laboratory testing. The present disclosure also finds use where it is desirable to provide a flow cytometer with improved cell sorting accuracy, enhanced particle collection, systems which provide alerts regarding component malfunction (e.g., clogged flow cell nozzle), reduced energy consumption, particle charging efficiency, more accurate particle charging and enhanced particle deflection during cell sorting. In embodiments, the present disclosure reduces the need for user input or manual adjustment during sample analysis with a flow cytometer. In certain embodiments, the subject systems provide fully automated protocols so that adjustments to a flow cytometer during use require little, if any human input.

The present disclosure also finds use in applications where cells prepared from a biological sample may be desired for research, laboratory testing or for use in therapy. In some embodiments, the subject methods and devices may facilitate the obtaining individual cells prepared from a target fluidic or tissue biological sample. For example, the subject methods and systems facilitate obtaining cells from fluidic or tissue samples to be used as a research or diagnostic specimen for diseases such as cancer. Likewise, the subject methods and systems facilitate obtaining cells from fluidic or tissue samples to be used in therapy. Methods and devices of the present disclosure allow for separating and collecting cells from a biological sample (e.g., organ, tissue, tissue fragment, fluid) with enhanced efficiency and low cost as compared to traditional flow cytometry systems.

Notwithstanding the appended clauses, the disclosure set forth herein is also defined by the following clauses:

1. A system comprising:

an imaging sensor configured to capture one or more images of a flow stream in a detection field of a flow cytometer; and a processor comprising memory operably coupled to the processor, wherein the memory includes instructions stored thereon to determine one or more properties of the flow stream and generate a data signal corresponding to the one or more properties of the flow stream,
wherein the processor is configured to automatically adjust one or more parameters of the flow cytometer in response to data signal.

2. The system according to clause 1, wherein the processor is configured to determine the spatial position of the flow stream and generate a data signal corresponding to the spatial position of the flow stream from the one or more images.

3. The system according to any of clauses 1-2, wherein the system further comprises a support stage positioned downstream from the detection field.

4. The system according to clause 3, wherein the system is configured to automatically adjust the position of the support stage in response to the data signal corresponding to the spatial position of the flow stream in the detection field.

5. The system according to clause 4, wherein the system is configured to adjust the position of the support stage in two dimensions.

6. The system according to any of clauses 3-5, wherein the support stage comprises a laser.

7. The system according to any of clauses 3-5, wherein the support stage comprises a container.

8. The system according to clause 7, wherein the system is configured to automatically align the container with the determined spatial position of the flow stream.

9. The system according to clause 8, wherein automatically aligning the container with the flow stream comprises:
mapping the position of the flow stream in the detection field in an X-Y plane;
mapping the position of the container in the X-Y plane; and
matching the position of the container with the position of the flow stream in the X-Y plane.

10. The system according to any of clauses 1-9, wherein the system further comprises:
a second imaging sensor configured to capture one or more images of the flow stream in a second detection field; and
a processor comprising memory operably coupled to the processor, wherein the memory includes instructions stored thereon to determine one or more properties of the flow stream in the second detection field and generate a second data signal corresponding to the one or more properties of the flow stream in the second detection field.

11. The system according to clause 10, wherein the processor is configured to determine the spatial position of the flow stream in the second detection field and generate a second data signal corresponding to the spatial position of the flow stream in the second detection field.

12. The system according to clause 11, wherein the system further comprises a second support stage positioned downstream from the first support stage.

13. The system according to clause 12, wherein the system is configured to automatically adjust the position of the second support stage in response to the first and second data signals.

14. The system according to clause 13, wherein the system is configured to adjust the position of the second support stage in two dimensions.

15. The system according to clause 13, wherein the second support stage comprises a container for collecting the flow stream.

16. The system according to clause 15, wherein the system is configured to automatically align the container with the determined spatial position of the flow stream in the second detection field.

17. The system according to clause 16, wherein automatically aligning the container comprises:
mapping the position of the flow stream in the second detection field in an X-Y plane;
mapping the position of the container in the X-Y plane; and
matching the position of the container with the position of the flow stream in the X-Y plane.

18. The system according to clause 1, wherein the processor is configured to determine the physical dimensions of the flow stream from the one or more images and generate a data signal corresponding to the physical dimensions of the flow stream.

19. The system according to clause 18, wherein the processor is configured to determine the width of the flow stream from the one or more images and generate a data signal corresponding to the width of the flow stream.

20. The system according to clause 19, wherein the processor is configured to determine flow cell nozzle orifice diameter and generate a data signal corresponding to the flow cell nozzle orifice diameter based on the determined width of the flow stream.

21. The system according to clause 20, wherein the processor is configured to automatically adjust one or more parameters of the flow cytometer based on the determined flow cell nozzle orifice diameter.

22. The system according to clause 21, wherein the parameters of the flow cytometer is selected from the group consisting of hydrostatic pressure, sheath fluid pressure, flow stream charge, deflection voltage, oscillator drive frequency, charge correction value, drop delay, drop frequency, drop amplitude and charge phase.

23. The system according to clause 22, wherein the processor is configured to automatically adjust sheath fluid pressure based on the determined flow cell nozzle orifice diameter.

24. The system according to clause 22, wherein the processor is configured to automatically adjust oscillator drive frequency based on the determined flow cell nozzle orifice diameter.

25. The system according to any of clauses 1-24, wherein the imaging sensor is a CCD camera.

26. A system for automatically localizing a stream position in a liquid flow from a flow cytometer comprising;
a first camera, adapted to detect a stream position in a first detection field and to generate a first signal representative of the stream position; and
a first stage wherein the first stage is operationally connected to the first camera and configured to move in an XY plane in response to the first signal.

27. The system of clause 26, further comprising a second camera adapted to detect a steam position in a second detection field and to generate a second signal representative of the stream position;
wherein the first and second detection fields of the first and second cameras are substantially orthogonally oriented in the XY plane; and
wherein the first stage is operationally connected to the second camera and configured to move the XY plane in response to the second signal in addition to the first signal.

28. The system according to any of clauses 26-27, wherein a laser is mounted on the first stage.

29. The system according to any of clauses 26-27, wherein a collection device is mounted on the first stage.
30. The system according to clause 26, further comprising a second stage wherein a collection device is mounted on the second stage and the second stage in configured to move in the XY plane in response to the first signal.
31. The system according to clause 30, further comprising a second stage wherein a collection device is mounted on the second stage the second stage is configured to move in the XY plane in response to the second signal in addition to the first signal.
32. The system according to clause 30, further comprising an electrical system configured to adjust an electrical charge on the flow stream in response to the second signal from the second camera.
33. The system according to clause 30, wherein the operational connection is mediated by a controller connected to the first camera and the first and second camera and the first stage and wherein the controller is configured to receive the signals from the first and second cameras and calculate an optimum position for the first stage.
34. The system according to clause 33, wherein the operational connection is mediated by a controller connected to the first and second camera and the second stage and configured to receive the signals from the first and second cameras and calculate an optimum position for the second stage.
35. The system according to any of clauses 26-34, wherein the stream is comprised of a series of drops.
36. A system for automatically determining a nozzle opening diameter comprising
a first camera, adapted to detect a stream dimension in a first detection field and to generate a first signal representative of the stream dimension;
a controller comprising a computer algorithm configured to determine a value for the nozzle opening diameter from the stream dimension and transmit the value to a flow cytometer.
37. The system according to clause 36, wherein the stream dimension is the width of the stream.
38. The system according to any of clauses 36-37, wherein the flow cytometer is configured to automatically adjust a series of parameters after receiving the transmitted value.
39. The system according to clause 38, wherein the series of parameters are selected from the group comprising hydrostatic pressure, drop charge, deflection voltage, charge correction value, drop delay, drop drive frequency, drop amplitude, and charge phase.
40. A method for adjusting one or more parameters of a flow cytometer, the method comprising:
capturing one or more images of a flow cytometer flow stream in a detection field;
determining one or more properties of the flow stream in the detection field;
generating a data signal corresponding to the one or more properties of the flow stream; and
adjusting one or more parameters of the flow cytometer in response to the data signal.
41. The method according to clause 40, wherein the method comprises determining the spatial position of the flow stream in the detection field and generating a data signal corresponding to the spatial position of the flow stream.
42. The method according to any of clauses 40-41, wherein the flow stream in the detection field is continuous.
43. The method according to clause 40, wherein the detection field comprises the flow stream upstream from the flow stream break-off point.
44. The method according to clause 43, wherein determining the spatial position of the flow stream comprises mapping the position of the flow stream in an X-Y plane.
45. The method according to clause 44, further comprising adjusting the position of a support stage in response to the data signal corresponding to the spatial position of the flow stream.
46. The method according to clause 45, wherein the support stage comprises a laser.
47. The method according to clause 45, wherein the support stage comprises a collection container.
48. The method according to clause 47, wherein the method comprises aligning the container with the determined spatial position of the flow stream.
47. The method according to clause 48, wherein aligning the container with the flow stream comprises:
mapping the position of the flow stream in the detection field in an X-Y plane;
mapping the position of the container in the X-Y plane; and
matching the position of the container with the position of the flow stream in the X-Y plane.
48. The method according any of clauses 40-47, wherein the method further comprises:
capturing one or more images of a flow cytometer flow stream in a second detection field;
determining one or more properties of the flow stream in the second detection field; and
generating a data signal corresponding to the one or more properties of the flow stream in the second detection field.
49. The method according to clause 48, wherein the method comprises determining the spatial position of the flow stream in the second detection field and generating a second data signal corresponding to the spatial position of the flow stream in the second detection field.
50. The method according to clause 48, wherein the flow stream in the second detection stream comprises discrete droplets.
51. The method according to clause 48, wherein the second detection field comprises the flow stream downstream from the flow stream break-off point.
52. The method according to clause 48, further comprising adjusting the position of a second support stage in response to the second data signal corresponding to the spatial position of the flow stream in the second detection field.
53. The method according to clause 48, wherein the method comprises adjusting the position of the second support stage in response to the first and second data signals.
54. The method according to clause 53, wherein the second support stage comprises a collection container.
55. The method according to clause 54, wherein the method comprises aligning the container with the determined spatial position of the flow stream in the second detection field.
56. The method according to clause 55, wherein aligning the container comprises:
mapping the position of the flow stream in the second detection field in an X-Y plane;
mapping the position of the container in the X-Y plane; and
matching the position of the container with the position of the flow stream in the X-Y plane.
57. The method according to clause 40, wherein the method comprises determining the physical dimensions of the flow stream in the detection field and generating a data signal corresponding to the physical dimensions of the flow stream.
58. The method according to clause 57, wherein the method comprises determining the width of the flow stream from the one or more images and generating a data signal corresponding to the width of the flow stream.
59. The method according to clause 58, further comprising determining the flow cell orifice diameter and generating a data signal corresponding to the flow cell nozzle orifice diameter based on the determined width of the flow stream.
60. The method according to clause 59, further comprising adjusting one or more parameters of the flow cytometer based on the determined flow cell nozzle orifice diameter.
61. The method according to clause 60, wherein the parameters of the flow cytometer is selected from the group consisting of hydrostatic pressure, sheath fluid pressure, flow stream charge, deflection voltage, oscillator drive frequency, charge correction value, drop delay, drop drive frequency, drop amplitude and charge phase.
62. The method according to clause 61, further comprising adjusting the drop drive frequency in response to the determined flow cell nozzle orifice diameter.
63. The method according to clause 62, further comprising adjusting the sheath fluid pressure in response to the determined flow cell nozzle orifice diameter.
64. A method comprising:
capturing one or more images of a flow cytometer flow stream in a detection field;
determining that the flow stream is not present in the captured image;
assessing parameters of the flow cytometer inputted by a user to determine if the flow stream is expected to be present in the captured image; and
generating an alert to the user indicating a flow cytometer malfunction.
65. The method according to clause 64, wherein the malfunction is a clogged nozzle.
66. The method according to clause 64, wherein the detection field comprises flow stream upstream from the flow stream break-off point.
67. The method according to clause 64, wherein the flow stream in the detection stream is continuous.
68. The method according to clause 64, further comprising inputting that the flow cytometer comprises an open flow cell nozzle orifice.
69. A method for adjusting one or more parameters of a flow cytometer, the method comprising:
injecting a sample into the sample port of a flow cytometer, wherein the flow cytometer comprises a system comprising a processor with memory operably coupled to the processor wherein the system is automated to:
capture one or more images of a flow cytometer flow stream comprising the sample in a detection field;
determine one or more properties of the flow stream in the detection field;
generate a data signal corresponding to the one or more properties of the flow stream; and
adjust one or more parameters of the flow cytometer in response to the data signal.
70. The method according to clause 69, wherein the method comprises determining the spatial position of the flow stream in the detection field and generating a data signal corresponding to the spatial position of the flow stream.
71. The method according to clause 69, wherein the flow stream in the detection stream is continuous.
72. The method according to clause 69, wherein the detection field comprises the flow stream upstream from the flow stream break-off point.
73. The method according to clause 72, wherein determining the spatial position of the flow stream comprises mapping the position of the flow stream in an X-Y plane.
74. The method according to clause 69, further comprising adjusting the position of a support stage in response to the data signal corresponding to the spatial position of the flow stream.
75. The method according to clause 74, wherein the support stage comprises a laser.
76. The method according to clause 74, wherein the support stage comprises a collection container.
77. The method according to clause 76, wherein the method comprises aligning the container with the determined spatial position of the flow stream.
78. The method according to clause 77, wherein aligning the container with the flow stream comprises:
mapping the position of the flow stream in the detection field in an X-Y plane;
mapping the position of the container in the X-Y plane; and
matching the position of the container with the position of the flow stream in the X-Y plane.
79. The method according clause 69, wherein the method further comprises:
capturing one or more images of a flow cytometer flow stream in a second detection field;
determining one or more properties of the flow stream in the second detection field; and
generating a data signal corresponding to the one or more properties of the flow stream in the second detection field.
80. The method according to clause 79, wherein the method comprises determining the spatial position of the flow stream in the second detection field and generating a second data signal corresponding to the spatial position of the flow stream in the second detection field.
81. The method according to clause 80, wherein the flow stream in the second detection stream comprises discrete droplets.
82. The method according to clause 80, wherein the second detection field comprises the flow stream downstream from the flow stream break-off point.
83. The method according to clause 80, further comprising adjusting the position of a second support stage in response to the second data signal corresponding to the spatial position of the flow stream in the second detection field.
84. The method according to clause 79, wherein the method comprises adjusting the position of the second support stage in response to the first and second data signals.
85. The method according to clause 84, wherein the second support stage comprises a collection container.
86. The method according to clause 85, wherein the method comprises aligning the container with the determined spatial position of the flow stream in the second detection field.
87. The method according to clause 86, wherein aligning the container comprises:
mapping the position of the flow stream in the second detection field in an X-Y plane;
mapping the position of the container in the X-Y plane; and
matching the position of the container with the position of the flow stream in the X-Y plane.

88. The method according to clause 69, wherein the method comprises determining the physical dimensions of the flow stream in the detection field and generating a data signal corresponding to the physical dimensions of the flow stream.
89. The method according to clause 88, wherein the method comprises determining the width of the flow stream from the one or more images and generating a data signal corresponding to the width of the flow stream.
90. The method according to clause 89, further comprising determining the flow cell orifice diameter and generating a data signal corresponding to the flow cell nozzle orifice diameter based on the determined width of the flow stream.
91. The method according to clause 90, further comprising adjusting one or more parameters of the flow cytometer based on the determined flow cell nozzle orifice diameter.
92. The method according to clause 91, wherein the parameters of the flow cytometer is selected from the group consisting of hydrostatic pressure, sheath fluid pressure, flow stream charge, deflection voltage, oscillator drive frequency, charge correction value, drop delay, drop frequency, drop amplitude and charge phase.
93. The method according to clause 92, further comprising adjusting the oscillator drive frequency in response to the determined flow cell nozzle orifice diameter.
94. The method according to clause 92, further comprising adjusting the sheath fluid pressure in response to the determined flow cell nozzle orifice diameter.
95. A system for configuring a flow cytometer, the system comprising:
a processor comprising memory operably coupled to the processor, wherein the memory includes instructions stored thereon, the instructions comprising:
  instructions for capturing one or more images of a flow cytometer flow stream in a detection field;
  algorithm for determining one or more properties of the flow stream in the detection field;
  algorithm for generating a data signal corresponding to the one or more properties of the flow stream; and
  instructions for adjusting one or more parameters of the flow cytometer in response to the data signal.
96. The system according to clause 95, wherein the memory comprises algorithm determining the spatial position of the flow stream in the detection field and generating a data signal corresponding to the spatial position of the flow stream.
97. The system according to clause 95, wherein the flow stream in the detection stream is continuous.
98. The system according to clause 95, wherein the detection field comprises the flow stream upstream from the flow stream break-off point.
99. The system according to clause 95, wherein the memory comprises algorithm for determining the spatial position of the flow stream comprises mapping the position of the flow stream in an X-Y plane.
100. The system according to clause 95, wherein the memory comprises algorithm for adjusting the position of a support stage in response to the data signal corresponding to the spatial position of the flow stream.
101. The system according to clause 100, wherein the support stage comprises a collection container.
102. The system according to clause 101, wherein the memory comprises algorithm for aligning the container with the determined spatial position of the flow stream.
103. The system according to clause 102, wherein aligning the container with the flow stream comprises:
  mapping the position of the flow stream in the detection field in an X-Y plane;
  mapping the position of the container in the X-Y plane; and
  matching the position of the container with the position of the flow stream in the X-Y plane.
104. The system according to clause 95, wherein the memory further comprises:
  instructions for capturing one or more images of a flow cytometer flow stream in a second detection field;
  algorithm for determining one or more properties of the flow stream in the second detection field; and
  algorithm for generating a data signal corresponding to the one or more properties of the flow stream in the second detection field.
105. The system according to clause 104, wherein the memory comprises algorithm for determining the spatial position of the flow stream in the second detection field and generating a second data signal corresponding to the spatial position of the flow stream in the second detection field.
106. The system according to clause 104, wherein the flow stream in the second detection stream comprises discrete droplets.
107. The system according to clause 104, wherein the second detection field comprises the flow stream downstream from the flow stream break-off point.
108. The system according to clause 104, wherein the memory further comprises algorithm for adjusting the position of a second support stage in response to the second data signal corresponding to the spatial position of the flow stream in the second detection field.
109. The system according to clause 104, where the memory comprises algorithm for aligning a container on the second support stage with the determined spatial position of the flow stream in the second detection field.
110. The system according to clause 109, wherein aligning the container comprises:
  mapping the position of the flow stream in the second detection field in an X-Y plane;
  mapping the position of the container in the X-Y plane; and
  matching the position of the container with the position of the flow stream in the X-Y plane.
111. The system according to clause 95, wherein the memory comprises algorithm for determining the physical dimensions of the flow stream in the detection field and generating a data signal corresponding to the physical dimensions of the flow stream.
112. The system according to clause 111, wherein the physical dimension is the width of the flow stream.
113. The system according to clause 111, wherein the memory further comprises algorithm for determining the flow cell orifice diameter and generating a data signal corresponding to the flow cell nozzle orifice diameter based on the determined width of the flow stream.
114. The system according to clause 113, wherein the memory further comprises algorithm for adjusting one or more parameters of the flow cytometer based on the determined flow cell nozzle orifice diameter.
115. The system according to clause 114, wherein the one or more parameters are selected from the group consisting of hydrostatic pressure, sheath fluid pressure, flow stream charge, deflection voltage, oscillator drive frequency, charge correction value, drop delay, drop frequency, drop amplitude and charge phase.

116. A system for configuring a flow cytometer, the system comprising:
a processor comprising memory operably coupled to the processor, wherein the memory includes instructions stored thereon, the instructions comprising:
instructions for capturing one or more images of a flow cytometer flow stream in a detection field;
algorithm for determining that the flow stream is not present in the captured image;
algorithm for assessing parameters of the flow cytometer inputted by a user to determine if the flow stream is expected to be present in the captured image; and
instructions for generating an alert to the user indicating a flow cytometer malfunction.

117. The system according to clause 116, wherein the malfunction is a clogged nozzle.

118. The system according to clause 116, wherein the detection field comprises flow stream upstream from the flow stream break-off point.

119. The system according to clause 116, wherein the flow stream in the detection stream is continuous.

120. The system according to clause 116, wherein the inputted parameter comprises indicating that the flow cytometer comprises an open flow cell nozzle orifice.

Although the foregoing invention has been described in some detail by way of illustration and example for purposes of clarity of understanding, it is readily apparent to those of ordinary skill in the art in light of the teachings of this disclosure that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method for adjusting one or more parameters of a flow cytometer, the method comprising:
injecting a sample into a flow cell of a flow cytometer, wherein the flow cytometer comprises a system comprising a processor with memory operably coupled to the processor wherein the system is automated to:
capture one or more images of the flow cytometer flow stream comprising the sample in a detection field;
determine the width of the flow stream in the detection field;
generate a data signal corresponding to a ratio of the determined width of the flow stream and a width of the flow stream that is expected based on nozzle orifice size of the flow cell; and
adjust one or more parameters of the flow cytometer in response to the data signal.

2. The method according to claim 1, wherein the one or more parameters of the flow cytometer is selected from the group consisting of hydrostatic pressure, sheath fluid pressure, flow stream charge, deflection voltage, drop drive frequency, charge correction value, drop delay, drop amplitude and charge phase.

3. The method according to claim 2, wherein the processor is configured to adjust sheath fluid pressure based on the determined flow cell nozzle orifice diameter.

4. The method according to claim 2, wherein the processor is configured to adjust drop drive frequency based on the determined flow cell nozzle orifice diameter.

5. The method according to claim 1, wherein the processor is configured to determine the nozzle orifice diameter of the flow cell and generate a data signal corresponding to the flow cell nozzle orifice diameter based on the determined width of the flow stream.

6. The method according to claim 5, wherein the processor is configured to adjust one or more parameters of the flow cytometer based on the determined flow cell nozzle orifice diameter.

7. The method according to claim 1, wherein the images of the flow cytometer flow stream are captured with a charge-coupled device (CCD) camera.

8. The method according to claim 1, wherein the width of the flow stream is determined from the images based on droplet volume.

9. The method according to claim 1, wherein the images of the flow stream are captured at the break-off point of the flow stream.

10. A flow cytometer comprising:
a flow cell configured to propagate a sample in a flow stream;
a sensor configured to capture one or more images of the flow stream;
a processor comprising memory operably coupled to the processor, wherein the memory includes instructions stored thereon to determine the width of the flow stream from the one or more images, generate a data signal corresponding to a ratio of the determined width of the flow stream and a width of the flow stream that is expected based on nozzle orifice size of the flow cell, and automatically adjust one or more parameters of the flow cytometer in response to the data signal.

11. The flow cytometer according to claim 10, wherein the parameters of the flow cytometer is selected from the group consisting of hydrostatic pressure, sheath fluid pressure, flow stream charge, deflection voltage, drop drive frequency, charge correction value, drop delay, drop amplitude and charge phase.

12. The flow cytometer according to claim 10, wherein the processor is configured to automatically adjust sheath fluid pressure based on the determined flow cell nozzle orifice diameter.

13. The flow cytometer according to claim 10, wherein the processor is configured to automatically adjust drop drive frequency based on the determined flow cell nozzle orifice diameter.

14. The flow cytometer according to claim 10, wherein the processor is configured to determine the nozzle orifice diameter of the flow cell and generate a data signal corresponding to the flow cell nozzle orifice diameter based on the determined width of the flow stream.

15. The flow cytometer according to claim 14, wherein the processor is configured to automatically adjust one or more parameters of the flow cytometer based on the determined flow cell nozzle orifice diameter.

16. The flow cytometer according to claim 10, wherein the sensor is a charge-coupled device (CCD) camera.

17. The flow cytometer according to claim 10, wherein the width of the flow stream is determined from the images based on droplet volume.

18. The flow cytometer according to claim 10, wherein the sensor is positioned at the break-off point of the flow stream.

* * * * *